(12) United States Patent
Amari et al.

(10) Patent No.: US 8,440,690 B2
(45) Date of Patent: May 14, 2013

(54) QUINUCLIDINE CARBONATE SALTS AND MEDICINAL COMPOSITION THEREOF

(75) Inventors: Gabriele Amari, Parma (IT); Maurizio Delcanale, Parma (IT)

(73) Assignee: Chiesi Farmaceutici S.p.A., Parma (IT)

( * ) Notice: Subject to any disclaimer, the term of this patent is extended or adjusted under 35 U.S.C. 154(b) by 0 days.

(21) Appl. No.: 13/219,109

(22) Filed: Aug. 26, 2011

(65) Prior Publication Data

US 2011/0319444 A1 Dec. 29, 2011

Related U.S. Application Data

(62) Division of application No. 12/512,262, filed on Jul. 30, 2009, now Pat. No. 8,039,483.

(30) Foreign Application Priority Data

Aug. 8, 2008 (EP) ................................ 08162066

(51) Int. Cl.
*A61K 31/439* (2006.01)
*A61P 11/00* (2006.01)

(52) U.S. Cl.
USPC ........................................................ 514/305

(58) Field of Classification Search ............ 514/305
See application file for complete search history.

(56) References Cited

U.S. PATENT DOCUMENTS

| | | | |
|---|---|---|---|
| 7,452,904 | B2 | 11/2008 | Catena Ruiz et al. |
| 7,838,534 | B2 | 11/2010 | Amari et al. |
| 8,039,483 | B2 | 10/2011 | Amari et al. |
| 2010/0173880 | A1 | 7/2010 | Caligiuri et al. |
| 2011/0308519 | A1 | 12/2011 | Schiaretti |
| 2011/0319444 | A1 | 12/2011 | Amari et al. |
| 2012/0101076 | A1 | 4/2012 | Patacchini et al. |
| 2012/0220557 | A1 | 8/2012 | Raschini et al. |
| 2012/0276018 | A1 | 11/2012 | Amari et al. |

FOREIGN PATENT DOCUMENTS

| | | |
|---|---|---|
| EP | 1 882 691 | 1/2008 |
| WO | 01/04118 | 1/2001 |
| WO | 02/096855 | 12/2002 |
| WO | 03/053966 | 7/2003 |

OTHER PUBLICATIONS

Gosen et al., Respiratory research, (2006), 7(73), pp. 1-15.*
Oenema et al., respiratory Research, (2010), 11(30), pp. 1-10.*
U.S. Appl. No. 13/165,930, filed Jun. 22, 2011, Amari, et al.
U.S. Appl. No. 13/165,936, filed Jun. 22, 2011, Amari, et al.
U.S. Appl. No. 13/165,948, filed Jun. 22, 2011, Amari, et al.
U.S. Appl. No. 13/232,415, filed Sep. 14, 2011, Amari, et al.
European Search Report issued in European Patent Application No. 08162066.8 on Jan. 29, 2009.

* cited by examiner

*Primary Examiner* — Niloofar Rahmani
(74) *Attorney, Agent, or Firm* — Oblon, Spivak, McClelland, Maier & Neustadt, L.L.P.

(57) ABSTRACT

Quinuclidine carbonate derivatives act as muscarinic receptor antagonists and are effective for the prevention and/or treatment of a broncho-obstructive or inflammatory diseases.

20 Claims, No Drawings

QUINUCLIDINE CARBONATE SALTS AND MEDICINAL COMPOSITION THEREOF

CROSS REFERENCES TO RELATED APPLICATIONS

This application is a Divisional Application of U.S. patent application Ser. No. 12/512,262, filed on Jul. 30, 2009, and claims priority to European Patent Application No. 08162066.8, filed on Aug. 8, 2008.

BACKGROUND OF THE INVENTION

1. Field of the Invention

The present invention relates to quinuclidine carbonate salts which act as muscarinic receptor antagonists. The present invention also relates to methods of preparing such a salt, compositions which contain such a salt, and methods of treating certain conditions by administering such a salt.

2. Discussion of the Background

Quaternary ammonium salts which act as muscarinic (M) receptors antagonists drugs are currently used in therapy to induce bronchodilation for the treatment of respiratory diseases. Examples of well known M receptor antagonists drugs are represented by ipratropium bromide and tiotropium bromide.

Several chemical classes acting as selective M3 receptors antagonists drugs have been developed for the treatment of inflammatory or obstructive airway diseases such as asthma and chronic obstructive pulmonary disease (COPD). Quinuclidine carbamate derivatives and their use as M3 antagonists are described in WO 02051841, WO 03053966, and WO 2008012290.

Said M and M3 receptors antagonists drugs are currently administered through inhalation in order to deliver the drug directly at the site of action and hence limiting the systemic exposure. However, even though the inhalatory route limits the systemic exposure, the known compounds may still exhibit undesired side effects due to systemic absorption.

It is hence highly desirable to provide M3 receptor antagonists drugs able to act locally, while having high potency and long duration of action, and said drugs, once adsorbed, are degraded to inactive compounds which are deprived of any systemic side effects typical of muscarinic antagonists.

SUMMARY OF THE INVENTION

Accordingly, it is one object of the present invention to provide novel M3 receptor antagonists drugs.

It is another object of the present invention to provide novel M3 receptor antagonists drugs which act locally.

It is another object of the present invention to provide novel M3 receptor antagonists drugs which exhibit a high potency and long duration of action.

It is another object of the present invention to provide novel M3 receptor antagonists drugs which, once adsorbed, are degraded to inactive compounds which are deprived of any systemic side effects typical of muscarinic antagonists.

It is another object of the present invention to provide novel methods of making such a M3 receptor antagonist.

It is another object of the present invention to provide novel compositions which contain such a M3 receptor antagonist.

It is another object of the present invention to provide novel methods of treating certain conditions or diseases by administering such a M3 receptor antagonist.

These and other objects, which will become apparent during the following detailed description, have been achieved by the inventors' discovery of quinuclidine carbonate salts represented by formula (I):

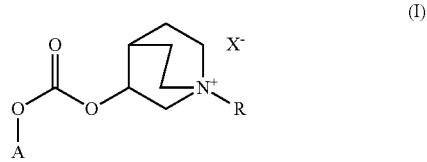

wherein:
A is optionally substituted aryl or heteroaryl or arylalkyl or heteroarylalkyl or a group represented by formula (a):

wherein
$R_3$ and $R_4$ are the same or different and may be independently selected from the group consisting of H, $(C_3$-$C_8)$-cycloalkyl, aryl or heteroaryl, wherein said aryl or heteroaryl may be optionally substituted with a halogen atom or with one or several substituents independently selected from the group consisting of OH, O—$(C_1$-$C_{10})$-alkyl, oxo (=O), SH, S—$(C_1$-$C_{10})$-alkyl, $NO_2$, CN, $CONH_2$, COOH, $(C_1$-$C_{10})$-alkoxycarbonyl, $(C_1$-$C_{10})$-alkylsulfanyl, $(C_1$-$C_{10})$-alkylsulfinyl, $(C_1$-$C_{10})$-alkylsulfonyl, $(C_1$-$C_{10})$-alkyl and $(C_1$-$C_{10})$-alkoxyl or when $R_3$ and $R_4$ are both independently aryl or heteroaryl they may be linked through a Y group which may be a $(CH_2)_n$ with n=0-2, wherein when n=0 Y is a single bond, forming a tricyclic ring system wherein the carbon atom of $(CH_2)_n$ may be substituted by a heteroatom selected from O, S, N and with the proviso that $R_3$ and $R_4$ are never both H;
R is a residue selected from $(C_1$-$C_{10})$-alkyl, $(C_2$-$C_{10})$-alkenyl, and $(C_2$-$C_{10})$-alkynyl optionally substituted with a group selected from:
$NH_2$, $NR_1R_2$, $CONR_1R_2$, $NR_2COR_1$, OH, $SOR_1$, $SO_2R_1$, SH, CN, $NO_2$, an alicyclic compound, Z—$R_1$ (wherein Z is selected from CO, O, COO, OCO, $SO_2$, S, SO, COS and SCO or it is a bond), and $(C_3$-$C_8)$-cycloalkyl, wherein
$R_1$ is a residue selected from:
an alicyclic compound optionally substituted with one or several substituents independently selected from OH, oxo (=O), SH, $NO_2$, CN, $CONH_2$, $NR_2CO$—$(C_1$-$C_x)$-alkyl, COOH, $(C_1$-$C_{10})$-alkoxycarbonyl, $(C_1$-$C_{10})$-alkylsulfanyl, $(C_1$-$C_{10})$-alkylsulfinyl, $(C_1$-$C_{10})$-alkylsulfonyl, $(C_1$-$C_{10})$-alkyl, and $(C_1$-$C_{10})$-alkoxyl $NR_2CO$—$(C_1$-$C_{10})$-alkyl;
aryl optionally substituted with $NR_2CO$—$(C_1$-$C_{10})$-alkyl, $(C_1$-$C_{10})$-alkyl, O—$(C_1$-$C_{10})$-alkyl or halogen, and
heteroaryl optionally substituted with $NR_2CO$—$(C_1$-$C_{10})$-alkyl or halogen, wherein
$R_2$ is a group selected from H, phenoxycarbonyl, benzyloxycarbonyl, $(C_1$-$C_{10}$-alkoxycarbonyl, $(C_1$-$C_{10})$-alkylcarbonyl, $(C_1$-$C_{10})$-alkylsulfonyl, and $(C_1$-$C_{10})$-alkyl; and
$X^-$ is a physiologically acceptable anion.

The present invention also provides pharmaceutical compositions which contain a salt represented by formula (I) alone or in combination with or in mixture with one or more pharmaceutically acceptable carriers and/or excipients.

The present invention also provides the use of a salt represented by formula (I) for preparing a medicament.

In a further aspect, the invention provides the use of a salt represented by formula (I) for the prevention and/or treatment of any broncho-obstructive or inflammatory disease, preferably asthma or chronic bronchitis or chronic obstructive pulmonary disease (COPD).

In a further aspect, the present invention provides the use of a salt represented by formula (I) for the manufacture of a medicament for the prevention and/or treatment of any broncho-obstructive or inflammatory disease, preferably asthma or chronic bronchitis or chronic obstructive pulmonary disease (COPD).

The present invention further provides a method for prevention and/or treatment of any broncho-obstructive or inflammatory disease, preferably asthma or chronic bronchitis or chronic obstructive pulmonary disease (COPD), which comprises administering to a subject in need thereof a therapeutically effective amount of a salt represented by formula (I).

The present invention also provides pharmaceutical compositions suitable for administration by inhalation.

Inhalable preparations include inhalable powders, propellant-containing metering aerosols or propellant-free inhalable formulations.

The present invention is also directed to devices which may be a single- or multi-dose dry powder inhaler, a metered dose inhaler and a soft mist nebulizer and which contain a salt represented by formula (I).

The present invention is also directed to a kit comprising a pharmaceutical composition which contains a salt represented by formula (I) alone or in combination with or in admixture with one or more pharmaceutically acceptable carriers and/or excipients and a device which may be a single- or multi-dose dry powder inhaler, a metered dose inhaler and a soft mist nebulizer and which contains a salt represented by general formula (I).

Thus, the present invention provides quinuclidine carbonate salts with therapeutically desirable characteristics. The salts represented by general formula (I) behave as soft-drugs, since they are able to produce a persistent bronchodilating effect in the lung but are consistently and rapidly transformed into inactive metabolites after passing into human plasma. This behaviour gives great advantages in terms of safety.

DETAILED DESCRIPTION OF THE PREFERRED EMBODIMENTS

The term "halogen atoms" as used herein includes fluorine, chlorine, bromine, and iodine.

The expression "$(C_1-C_{10})$ alkyl", refers to straight-chained and branched alkyl groups wherein the number of carbon atoms is from 1 to 10. Examples of groups are methyl, ethyl, n-propyl, isopropyl, t-butyl, pentyl, hexyl, heptyl, octanyl, nonenyl, and decenyl.

Optionally, one or more hydrogen atoms in said groups can be replaced by halogen atoms. The derived expressions "$(C_1-C_{10})$-alkoxycarbonyl", "$(C_1-C_{10})$-alkylsulfanyl", "$(C_1-C_{10})$-alkylsulfinyl", "$(C_1-C_{10})$-alkylsulfonyl" and "$(C_1-C_{10})$-alkoxyl" are to be construed in an analogous manner.

The derived expressions "$(C_2-C_{10})$ alkenyl" and "$(C_2-C_{10})$ alkynyl", are to be construed in an analogous manner.

The expression "an alicyclic compound" includes:

"$(C_3-C_8)$-cycloalkyl", which refers to cyclic non-aromatic isolated hydrocarbon saturated groups. Examples include cyclopropyl, cyclobutyl, cyclopentyl, cyclohexyl, cycloheptyl, and cyclooctenyl;

"bicycloalkyl" and "tricycloalkyl" groups which are non-aromatic saturated cyclic alkyl moieties consisting of two or three rings, respectively, wherein said rings share at least one carbon atom. For purposes of the present invention, and unless otherwise indicated, bicycloalkyl groups include spiro rings and fused rings. Examples of bicycloalkyl groups include, but are not limited to, bicyclo-[3.1.0]-hexyl, bicyclo-[2.2.1]-hept-1-yl, norbornyl, spiro[4.5]decyl, Spiro[4.4]nonyl, Spiro [4.3]octyl, and Spiro[4.2]heptyl. An example of a tricycloalkyl group is adamantanyl; and cyclic non-aromatic hydrocarbon unsaturated groups. Examples include cyclohexenyl, norbornenyl, bicyclo [2.2.1.]heptanyl.

Optionally, one or more hydrogen atoms in said groups can be replaced by one or more halogen atoms.

The expression "aryl" refers to mono, bi- or tricyclic ring systems having 5 to 20, preferably from 5 to 15, ring atoms, and wherein at least one ring is aromatic. Optionally, one or more hydrogen atoms in said rings can be replaced by one or more halogen atoms or phenyl.

The expression "heteroaryl" refers to mono, bi- or tricyclic ring systems having 5 to 20, preferably from 5 to 15, ring atoms, in which at least one ring is aromatic and in which at least one ring atom is a heteroatom (e.g. N, S, or O). Optionally, one or more hydrogen atoms in said rings can be replaced by one or more halogen atoms.

The expression "arylalkyl" refers to a "$(C_1-C_4)$ alkyl" optionally substituted by a mono, bi- or tricyclic ring systems which have 5 to 20, preferably from 5 to 15, ring atoms. Optionally, one or more hydrogen atoms in said rings can be replaced by one or more halogen atoms.

Examples of suitable arylalkyl groups include benzyl, biphenylmethyl and thiophenylmethyl.

The expression "heteroarylalkyl" refers to a "$(C_1-C_4)$ alkyl" optionally substituted by a mono, bi- or tricyclic ring systems which have 5 to 20 ring atoms, preferably from 5 to 15, in which at least one ring is aromatic and in which at least one ring atom is a heteroatom (e.g. N, S or O). Optionally, one or more hydrogen atoms in said rings can be replaced by one or more halogen atoms.

Examples of suitable monocyclic systems include thiophene, cyclopentadiene, benzene, pyrrole, pyrazole, imidazole, isoxazole, oxazole, isothiazole, thiazole, pyridine, imidazolidine, piperidine, and furan radicals.

Examples of suitable bicyclic systems include naphthalene, biphenyl, purine, pteridine, benzotriazole, quinoline, isoquinoline, indole, isoindole, and benzothiophene radicals.

Examples of suitable tricyclic systems include fluorene radicals.

The invention is directed to quinuclidine carbonate salts which act as muscarinic receptors antagonists, said salts preferably acting on the M3 receptors.

Advantageously, physiologically acceptable anions X include those selected from the group consisting of chloride, bromide, iodide, sulfate, phosphate, methanesulfonate, nitrate, maleate, acetate, citrate, fumarate, tartrate, oxalate, succinate, benzoate, and p-toluenesulfonate, preferably chloride, bromide and iodide, more preferably chloride and bromide.

A preferred group of salts of formula (I) is that wherein R is $(C_1-C_6)$-alkyl substituted by —Z—$R_1$, wherein Z and $R_1$ are as described above.

Another preferred group of salts of formula (I) is that wherein R is $(C_1-C_6)$-alkyl substituted by —Z—$R_1$, wherein Z is O, CO or a bond and $R_1$ is aryl or heteroaryl as described above, preferably substituted with one or more halogen atoms.

A more preferred group of salts of formula (I) is that wherein R is $CH_2$, Z is CO and $R_1$ is thienyl, according to formula (II):

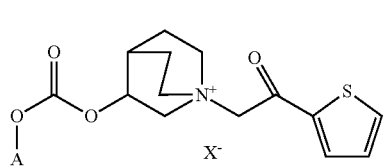

wherein A is as defined above.

A first group of salts of formula (II) is represented by the salts wherein A is optionally substituted aryl or heteroaryl or arylalkyl or heteroarylalkyl or a group of formula (a)

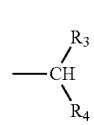

wherein $R_3$ and $R_4$ are both independently aryl or heteroaryl, preferably substituted with one or more halogen atoms.

A second group of salts of formula (II) is represented by the salts wherein A is a group of formula (a), wherein $R_3$ and $R_4$ are both phenyl, preferably substituted with one or more halogen atoms.

A third group of salts of formula (II) is represented by the salts wherein A is a compound of formula (a), wherein $R_3$ and $R_4$ are both independently phenyl and they are linked through a Y group which may be a $(CH_2)_n$ with n=0-2, wherein when n=0, Y is a single bond, forming a tricyclic ring system of formula (b), wherein the carbon atom of $(CH_2)_n$ may be substituted by a heteroatom selected from O, S, N.

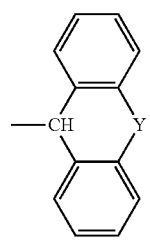

A fourth group of salts of formula (II) is represented by the salts wherein A is a 9H-fluoren-9-yl, preferably substituted with one or more halogen atoms.

A fifth group of salts of formula (II) is represented by the salts wherein A is an arylalkyl, preferably a phenyl-$(C_1-C_4)$-alkyl, more preferably substituted with one or more halogen atoms and even more preferably A is a benzyl, optionally substituted with one or more halogen atoms.

A sixth group of salts of formula (II) is represented by the salts wherein A is a biphenylmethyl, preferably substituted with one or more halogen atoms.

A seventh group of salts of formula (II) is represented by the salts wherein A is a thiophenylmethyl, preferably substituted with one or more halogen atoms.

Another preferred group of salts of formula (I) is that wherein R is a propyl substituted by —Z—$R_1$ group wherein Z is O and $R_1$ is phenyl, according to formula (III):

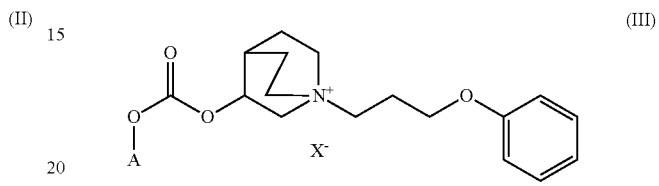

wherein A is as defined above.

A first group of salts of formula (III) is represented by the salts wherein A is optionally substituted aryl or heteroaryl or arylalkyl or heteroarylalkyl or a group of formula (a)

wherein $R_3$ and $R_4$ are both independently aryl or heteroaryl, preferably substituted with one or more halogen atoms.

A second group of salts of formula (III) is represented by the salts wherein A is a group of formula (a), wherein $R_3$ and $R_4$ are both phenyl, preferably substituted with one or more halogen atoms.

A third group of salts of formula (III) is represented by the salts wherein A is a group of formula (a), wherein $R_3$ and $R_4$ are both phenyl and they are linked through a Y group which may be a $(CH_2)_n$ with n=0-2, wherein when n=0, Y is a single bond, forming a tricyclic ring system of formula (b), wherein the carbon atom of $(CH_2)_n$ may be substituted by a heteroatom selected from O, S, N.

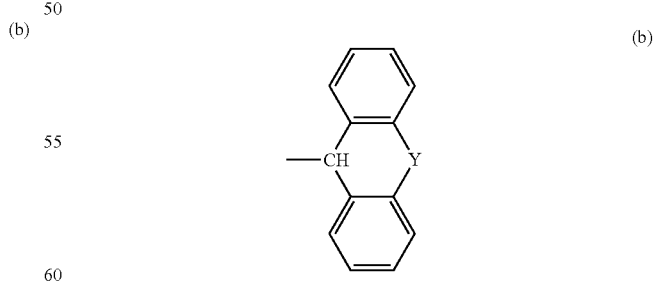

A fourth group of salts of formula (III) is represented by the salts wherein A is a 9H-fluoren-9-yl, preferably substituted with one or more halogen atoms.

A fifth group of salts of formula (III) is represented by the salts wherein A is arylalkyl, preferably a phenyl-$(C_1-C_4)$-alkyl, more preferably substituted with one or more halogen atoms and even more preferably A is a benzyl, optionally substituted with one or more halogen atoms.

A sixth group of salts of formula (III) is represented by the salts wherein A is a biphenylmethyl, preferably substituted with one or more halogen atoms.

A seventh group of salts of formula (III) is represented by the salts wherein A is a thiophenylmethyl, preferably substituted with one or more halogen atoms.

Another preferred group of salts of formula (I) is that wherein R is a methyl substituted by —Z—$R_1$ group wherein Z is CO and $R_1$ is phenyl, according to formula (IV):

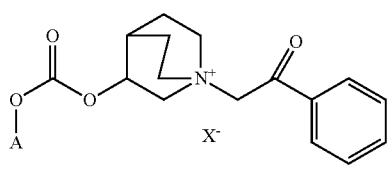

(IV)

Another preferred group of salts of formula (I) is that wherein R is a methyl substituted by —Z—$R_1$ group wherein Z is CO and $R_1$ is thienyl, according to formula (V):

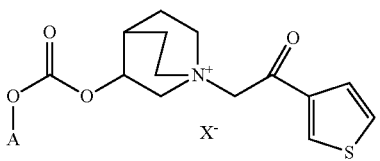

(V)

It will be apparent that the salts of formula (I) may contain asymmetric centers. Therefore the invention also includes the optical stereoisomers and mixtures thereof.

Where the compounds according to the invention have at least one asymmetric center, they may exist as enantiomers. Where the compounds according to the invention possess two or more asymmetric centers, they may additionally exist as diastereoisomers. It is to be understood that all such isomers and mixtures thereof in any proportion are encompassed within the scope of the present invention.

The active salts (I) shows at least one chiral center, which is represented by the quinuclidine carbon atom bearing the carbonate group.

In the preferred embodiments, the active compound (I) is in the form of the substantially pure (R)-enantiomer, wherein the enantiomeric purity is higher than 85%, more preferably than 90%, more preferably than 95% and even more preferably than 99%.

According to specific embodiments, the present invention provides the compounds reported below:

| Compound | Chemical name |
|---|---|
| 1 | (R)-3-[bis-(3-fluoro-phenyl)-methoxycarbonyloxy]-1-(2-oxo-2-thiophen-2-yl-ethyl)-1-azonia-bicyclo[2.2.2]octane; chloride |
| 2 | (R)-3-Benzhydryloxycarbonyloxy-1-(2-oxo-2-thiophen-2-yl-ethyl)-1-azonia-bicyclo[2.2.2]octane; chloride |
| 3 | (R)-3-(9H-Fluoren-9-yloxycarbonyloxy)-1-(2-oxo-2-thiophen-2-yl-ethyl)-1-azonia-bicyclo[2.2.2]octane; chloride |
| 4 | (R)-3-(3-Fluoro-benzyloxycarbonyloxy)-1-(2-oxo-2-thiophen-2-yl-ethyl)-1-azonia-bicyclo[2.2.2]octane; chloride |
| 5 | (R)-3-(4-Fluoro-benzyloxycarbonyloxy)-1-(2-oxo-2-thiophen-2-yl-ethyl)-1-azonia-bicyclo[2.2.2]octane; chloride |
| 6 | (R)-3-(4-Bromo-benzyloxycarbonyloxy)-1-(2-oxo-2-thiophen-2-yl-ethyl)-1-azonia-bicyclo[2.2.2]octane; chloride; chloride |
| 7 | (R)-3-(Biphenyl-2-yloxycarbonyloxy)-1-(2-oxo-2-thiophen-2-yl-ethyl)-1-azonia-bicyclo[2.2.2]octane; chloride |
| 8 | (R)-3-(9H-Fluoren-9-yloxycarbonyloxy)-1-phenethyl-1-azonia-bicyclo[2.2.2]octane; bromide |
| 9 | (R)-1-Benzyl-3-(9H-fluoren-9-yloxycarbonyloxy)-1-azonia-bicyclo[2.2.2]octane; chloride |
| 10 | (R)-3-(9H-Fluoren-9-yloxycarbonyloxy)-1-methyl-1-azonia-bicyclo[2.2.2]octane; iodide |
| 11 | (R)-3-(9H-Fluoren-9-yloxycarbonyloxy)-1-(3-phenoxy-propyl)-1-azonia-bicyclo[2.2.2]octane; bromide |
| 12 | (R)-3-(Biphenyl-2-yloxycarbonyloxy)-1-(3-phenoxy-propyl)-1-azonia-bicyclo[2.2.2]octane; bromide |
| 13 | (R)-3-(Biphenyl-2-yloxycarbonyloxy)-1-methyl-1-azonia-bicyclo[2.2.2]octane; iodide |
| 14 | (R)-1-(2-Oxo-2-thiophen-2-yl-ethyl)-3-(thiophen-2-ylmethoxycarbonyloxy)-1-azonia-bicyclo[2.2.2]octane; chloride |
| 15 | (R)-3-[Bis-(4-chloro-phenyl)-methoxycarbonyloxy]-1-(2-oxo-2-thiophen-2-yl-ethyl)-1-azonia-bicyclo[2.2.2]octane; chloride |
| 16 | (R)-3-[Bis-(4-bromo-phenyl)-methoxycarbonyloxy]-1-(2-oxo-2-thiophen-2-yl-ethyl)-1-azonia-bicyclo[2.2.2]octane; chloride |
| 17 | (R)-3-[Bis-(4-fluoro-phenyl)-methoxycarbonyloxy]-1-(2-oxo-2-thiophen-2-yl-ethyl)-1-azonia-bicyclo[2.2.2]octane; chloride |
| 18 | (R)-3-(3-Bromo-benzyloxycarbonyloxy)-1-(2-oxo-2-thiophen-2-yl-ethyl)-1-azonia-bicyclo[2.2.2]octane; chloride |
| 19 | (R)-3-[Bis-(3-fluoro-phenyl)-methoxycarbonyloxy]-1-(2-oxo-2-phenyl-ethyl)-1-azonia-bicyclo[2.2.2]octane; bromide |
| 20 | (R)-3-[Bis-(3-fluoro-phenyl)-methoxycarbonyloxy]-1-carbamoylmethyl-1-azonia-bicyclo[2.2.2]octane; bromide |
| 21 | (R)-3-[Bis-(3-fluoro-phenyl)-methoxycarbonyloxy]-1-(2-oxo-2-p-tolyl-ethyl)-1-azonia-bicyclo[2.2.2]octane; bromide |
| 22 | (R)-3-[Bis-(3-fluoro-phenyl)-methoxycarbonyloxy]-1-[2-(4-fluoro-phenyl)-2-oxo-ethyl]-1-azonia-bicyclo[2.2.2]octane; bromide |
| 23 | (R)-3-[Bis-(3-fluoro-phenyl)-methoxycarbonyloxy]-1-[2-(4-methoxy-phenyl)-2-oxo-ethyl]-1-azonia-bicyclo[2.2.2]octane; bromide |
| 24 | (R)-3-[Bis-(3-fluoro-phenyl)-methoxycarbonyloxy]-1-(2-oxo-2-thiophen-3-yl-ethyl)-1-azonia-bicyclo[2.2.2]octane; bromide |
| 25 | (R)-3-[Bis-(3-fluoro-phenyl)-methoxycarbonyloxy]-1-phenylcarbamoylmethyl-1-azonia-bicyclo[2.2.2]octane; bromide |
| 26 | (R)-3-[Bis-(3-fluoro-phenyl)-methoxycarbonyloxy]-1-[2-(5-chloro-thiophen-2-yl)-2-oxo-ethyl]-1-azonia-bicyclo[2.2.2]octane; bromide |
| 27 | (R)-3-[Bis-(3-fluoro-phenyl)-methoxycarbonyloxy]-1-[2-(3,5-dibromo-thiophen-2-yl)-2-oxo-ethyl]-1-azonia-bicyclo[2.2.2]octane; chloride |
| 28 | (R)-3-[Bis-(3-fluoro-phenyl)-methoxycarbonyloxy]-1-(2-oxo-2-thiazol-2-yl-ethyl)-1-azonia-bicyclo[2.2.2]octane; bromide |
| 29 | (R)-3-[Bis-(3-fluoro-phenyl)-methoxycarbonyloxy]-1-(2-oxo-2-o-tolyl-ethyl)-1-azonia-bicyclo[2.2.2]octane; bromide |
| 30 | (R)-3-[Bis-(3-fluoro-phenyl)-methoxycarbonyloxy]-1-(2-oxo-2-m-tolyl-ethyl)-1-azonia-bicyclo[2.2.2]octane; bromide |
| 31 | (R)-3-[Bis-(3-fluoro-phenyl)-methoxycarbonyloxy]-1-(4-methyl-pent-3-enyl)-1-azonia-bicyclo[2.2.2]octane; bromide |
| 32 | (R)-1-(2-Benzo[b]thiophen-2-yl-2-oxo-ethyl)-3-[bis-(3-fluoro-phenyl)-methoxycarbonyloxy]-1-azonia-bicyclo[2.2.2]octane; bromide |
| 33 | (R)-1-Benzyl-3-[bis-(3-fluoro-phenyl)-methoxycarbonyloxy]-1-azonia-bicyclo[2.2.2]octane; bromide |
| 34 | (R)-3-[Bis-(3-fluoro-phenyl)-methoxycarbonyloxy]-1-(2-phenoxy-ethyl)-1-azonia-bicyclo[2.2.2]octane; bromide |
| 35 | (R)-3-[Bis-(3-fluoro-phenyl)-methoxycarbonyloxy]-1-methyl-1-azonia-bicyclo[2.2.2]octane; iodide |
| 36 | (R)-3-[bis-(3-fluoro-phenyl)-methoxycarbonyloxy]-1-(2-oxo-2-pyridin-4-yl-ethyl)-1-azonia-bicyclo[2.2.2]octane; bromide |
| 37 | (R)-1-[(2-Fluoro-phenyl)-(3-fluoro-phenyl)-methoxycarbonyloxy]-1-(2-oxo-2-thiophen-2-yl-ethyl)-1-azonia-bicyclo[2.2.2]octane; chloride |
| 38 | (R)-3-[Bis-(2-chloro-phenyl)-methoxycarbonyloxy]-1-(2-oxo-2-thiophen-2-yl-ethyl)-1-azonia-bicyclo[2.2.2]octane; chloride |
| 39 | (R)-1-(2-Oxo-thiophen-2-yl-ethyl)-3-(phenyl-o-tolyl-methoxycarbonyloxy)-1-azonia-bicyclo[2.2.2]octane; chloride |
| 40 | (R)-3-[(3-Fluoro-phenyl)-(3-methoxy-phenyl)-methoxycarbonyloxy]-1-(2-oxo-2-thiophen-2-yl-ethyl)-1-azonia-bicyclo[2.2.2]octane; chloride |

| Com- pound | Chemical name |
|---|---|
| 41 | (R)-3-[Cyclohexyl-(3-fluoro-phenyl)-methoxycarbonyloxy]-1-(2-oxo-2-thiophen-2-yl-ethyl)-1-azonia-bicyclo[2.2.2]octane; chloride |
| 42 | (R)-3-[(3-Chloro-phenyl)-(3-fluoro-phenyl)-methoxycarbonyloxy]-1-(2-oxo-2-thiophen-2-yl-ethyl)-1-azonia-bicyclo[2.2.2]octane; chloride |
| 43 | (R)-3-[(3,5-Difluoro-phenyl)-(3-fluoro-phenyl)-methoxycarbonyloxy]-1-(2-oxo-2-thiophen-2-yl-ethyl)-1-azonia-bicyclo[2.2.2]octane; chloride |
| 44 | (R)-3-[(3-Fluoro-phenyl)-m-tolyl-methoxycarbonyloxy]-1-(2-oxo-2-thiophen-2-yl-ethyl)-1-azonia-bicyclo[2.2.2]octane; chloride |
| 45 | (R)-3-[(3-Fluoro-phenyl)-(4-methylsulfanyl-phenyl)-methoxycarbonyloxy]-1-(2-oxo-2-thiophen-2-yl-ethyl)-1-azonia-bicyclo[2.2.2]octane; chloride |
| 46 | (R)-3-[(3-Fluoro-phenyl)-(4-fluoro-phenyl)-methoxycarbonyloxy]-1-(2-oxo-2-thiophen-2-yl-ethyl)-1-azonia-bicyclo[2.2.2]octane; chloride |
| 47 | (R)-3-[(3,4-Difluoro-phenyl)-phenyl-methoxycarbonyloxy]-1-(2-oxo-2-thiophen-2-yl-ethyl)-1-azonia-bicyclo[2.2.2]octane; chloride |
| 48 | (R)-3-[(3-Fluoro-phenyl)-phenyl-methoxycarbonyloxy]-1-(2-oxo-2-thiophen-2-yl-ethyl)-1-azonia-bicyclo[2.2.2]octane; chloride |

The salts of formula (I) may be prepared according to known methods. Some of the processes which can be used are described below and reported in Scheme 1.

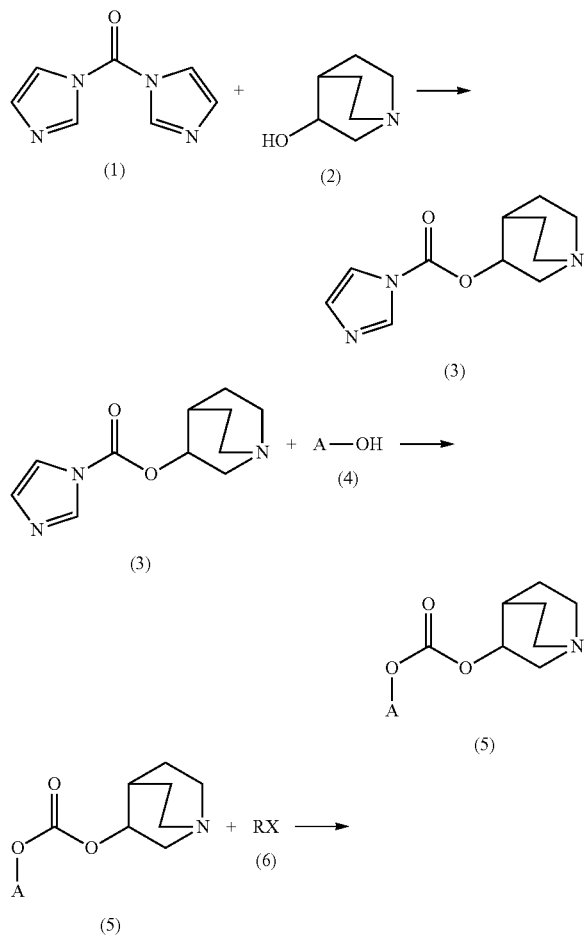

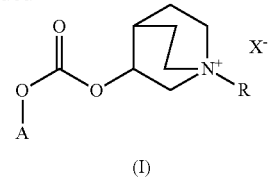

General procedure for the preparation of salts of formula (I).

The salts of general formula (I) may be prepared according to a general process which includes the following steps:

$1^{st}$ step—An amino-alcohol of formula (2) is reacted with 1,1'-carbonyldiimidazole (1) in an aprotic solvent. Advantageously, the reaction is carried out in a solvent selected from $CH_3CN$, $CH_2Cl_2$, $CHCl_3$, tetrahydrofuran (THF), and dioxane at a temperature ranging from 0° C. to the boiling point of the solvent. Water is added, and the imidazole derivative (3) is extracted with a solvent. Examples of solvents which can be suitably used are ethyl acetate, diethyl ether, methylene chloride;

$2^{nd}$ step—the solvent is evaporated to dryness, and the residue is reacted with an alcohol of formula (4) in an aprotic solvent. Advantageously, the solvent is selected from THF, dimethylformamide (DMF), and dimethylacetal (DMA). Preferably, the alcohol is activated with a base advantageously selected from NaH, BuLi (butyl lithium), and lithium diisopropylamide (LDA), to give a compound of formula (5).

$3^{rd}$ step—Compounds of formula (5) may be alkylated at the nitrogen atom of the tertiary amine by means of an alkylating agent RX wherein R is as previously defined and X is, according to known conditions, chlorine, bromine, or iodine, giving a quaternary ammonium salt of formula (I).

The invention also provides pharmaceutical compositions of salts of formula (I) in admixture with one or more pharmaceutically acceptable carriers, for example those described in Remington's Pharmaceutical Sciences Handbook, XVII Ed., Mack Pub., N.Y., U.S.A.

Administration of the compounds of the present invention may be accomplished according to patient needs, for example, orally, nasally, parenterally (subcutaneously, intravenously, intramuscularly, intrasternally and by infusion), by inhalation, rectally, vaginally, topically, locally, transdermally, and by ocular administration.

Various solid oral dosage forms can be used for administering compounds of the invention including such solid forms as tablets, gelcaps, capsules, caplets, granules, lozenges and bulk powders. The compounds of the present invention can be administered alone or combined with various pharmaceutically acceptable carriers, diluents (such as sucrose, mannitol, lactose, starches) and known excipients, including suspending agents, solubilizers, buffering agents, binders, disintegrants, preservatives, colorants, flavorants, lubricants and the like. Time release capsules, tablets and gels are also advantageous in administering the compounds of the present invention.

Various liquid oral dosage forms can also be used for administering compounds of the invention, including aqueous and non-aqueous solutions, emulsions, suspensions, syrups, and elixirs. Such dosage forms can also contain suitable known inert diluents such as water and suitable known excipients such as preservatives, wetting agents, sweeteners, flavorants, as well as agents for emulsifying and/or suspending the compounds of the invention. The salts of the present invention may be injected, for example, intravenously, in the form of an isotonic sterile solution. Other preparations are also possible.

Suppositories for rectal administration of the compounds of the invention can be prepared by mixing the compound with a suitable excipient such as cocoa butter, salicylates and polyethylene glycols.

Formulations for vaginal administration can be in the form of cream, gel, paste, foam, or spray formula containing, in addition to the active ingredient, such as suitable carriers, are also known.

For topical administration, the pharmaceutical composition can be in the form of creams, ointments, liniments, lotions, emulsions, suspensions, gels, solutions, pastes, powders, sprays, and drops suitable for administration to the skin, eye, ear or nose. Topical administration may also involve transdermal administration via means such as transdermal patches.

For the treatment of the diseases of the respiratory tract, the salts according to the invention are preferably administered by inhalation.

Inhalable preparations include inhalable powders, propellant-containing metering aerosols or propellant-free inhalable formulations.

For administration as a dry powder, single- or multi-dose inhalers known from the prior art may be utilized. In that case, the powder may be filled in gelatine, plastic or other capsules, cartridges or blister packs or in a reservoir.

A diluent or carrier, generally non-toxic and chemically inert to the salts of the present invention, e.g. lactose or any other additive suitable for improving the respirable fraction may be added to the powdered compounds of the invention.

Inhalation aerosols containing propellant gas such as hydrofluoroalkanes may contain the salts of the invention either in solution or in dispersed form. The propellant-driven formulations may also contain other ingredients such as co-solvents, stabilizers and optionally other excipients.

The propellant-free inhalable formulations comprising the salts of the invention may be in form of solutions or suspensions in an aqueous, alcoholic or hydroalcoholic medium and they may be delivered by jet or ultrasonic nebulizers known from the prior art or by soft-mist nebulizers such as Respimat®.

The salts of the invention may be administered as the sole active agent or in combination with other pharmaceutical active ingredients including those currently used in the treatment of respiratory disorders, e.g. beta$_2$-agonists, corticosteroids, and PDE4 inhibitors.

The dosages of the salts of the invention depend upon a variety of factors including the particular disease to be treated, the severity of the symptoms, the route of administration, the frequency of the dosage interval, the particular compound utilized, the efficacy, toxicology profile, and pharmacokinetic profile of the compound.

Advantageously, the salts of formula (I) can be administered for example, at a dosage comprised between 0.001 and 1000 mg/day, preferably between 0.1 and 500 mg/day.

When the salts of formula (I) are administered by inhalation route, they are preferably given at a dosage comprised between 0.001 and 500 mg/day, preferably between 0.1 and 200 mg/day.

The salts of formula (I) may be administered for the prevention and/or treatment of broncho-obstructive or inflammatory diseases, such as asthma, chronic bronchitis, chronic obstructive pulmonary disease (COPD), bronchial hyperreactivity, cough, emphysema or rhinitis; urological disorders such as urinary incontinence, pollakiuria, cystospasm, chronic cystitis and overactive bladder (OAB); gastrointestinal disorders such as bowel syndrome, spastic colitis, diverticulitis, peptic ulceration, gastrointestinal motility or gastric acid secretion; dry mouth; mydriasis, tachycardia; ophthalmic interventions cardiovascular disorders such as vagally induced sinus bradycardia.

Other features of the invention will become apparent in the course of the following descriptions of exemplary embodiments which are given for illustration of the invention and are not intended to be limiting thereof.

EXAMPLES

Example 1

Preparation of imidazole-1-carboxylic acid (R)-1-aza-bicyclo[2.2.2]oct-3-yl ester

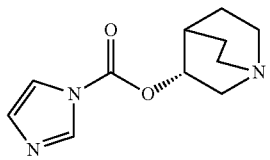 [SMILES: O=C(O[C@H]1CN2CCC1CC2)n1ccnc1]

Under a nitrogen atmosphere, 7.0 g (55.0 mmol) of (R)-3-quinuclidinol were suspended in 100 ml of CH$_2$Cl$_2$. After cooling the suspension to 0° C., a solution of 1,1'-carbonyldiimidazole (10.7 g, 66.0 mmol) in 150 mL of CH$_2$Cl$_2$ was added. The reaction mixture was stirred at 0° C. for 4 hours, then water was added (100 ml). The organic layer was separated, washed with water, dried over sodium sulphate and the solvent was evaporated under reduced pressure. The residue oil (13.1 g) was used without further purification.

Example 2

Preparation of carbonic acid (R)-1-aza-bicyclo[2.2.2]oct-3-yl ester bis-(3-fluoro-phenyl)-methyl ester

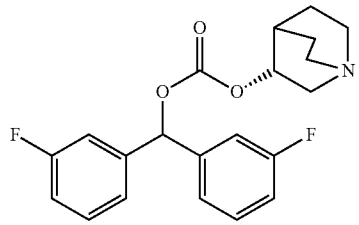

A solution of 3,3'-difluorobenzhydrol (1.1 g, 5 mmol) in dry THF (8 mL) was added to a solution of BuLi (butyl lithium) 2.5M in hexane (2.0 mL, 5 mmol) at 0° C.; after stirring for 30 minutes, a solution of imidazole-1-carboxylic acid (R)-1-aza-bicyclo[2.2.2]oct-3-yl ester (1.1 g, 5 mmol), obtained as described in example 1, in dry THF (16 ml) was added, and the mixture was stirred at 0° C. for 1.5 hours. Water (100 ml) was added, and the mixture was extracted with EtOAc (2×50 ml). The collected organic layers were dried over sodium sulphate and the solvent was evaporated under reduced pressure. The residue was purified by column chromatography on silica gel, eluting with CH$_2$Cl$_2$/MeOH=95/5. Fractions containing the product were combined and concentrated by evaporation to give 1.4 g, (75% yield) of the title compound as pale yellow oil.

$^1$H NMR analysis (300 MHz, DMSO-d6)

δ: 7.31 (m, 8H), 6.72 (s, 1H), 4.66 (m, 1H), 3.11 (m, 1H), 2.58 (m, 5H), 1.96 (d, 1H, J=2.98 Hz), 1.59 (m, 4H).

The following intermediates (Examples 3 to 13) were obtained with a process similar to the one used to prepare the compound of Example 2, by reacting the compound prepared in Example 1 with the suitable alcohols, such as benzhydrol, fluorenol, 3-fluoro-benzol, 4-fluoro-benzol, 4-bromo-benzol, 2-hydroxy biphenyl, 2-hydroxy methyl thiophene, bis-(4-chloro-phenol) or bis-(4-bromo-phenol).

Example 3

Carbonic acid (R)-1-aza-bicyclo[2.2.2]oct-3-yl ester benzhydryl ester

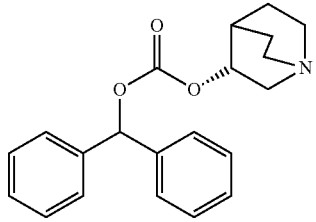

The desired product was prepared by reacting imidazole-1-carboxylic acid (R)-1-aza-bicyclo[2.2.2]oct-3-yl ester with benzhydrol.

Example 4

Carbonic acid (R)-1-aza-bicyclo[2.2.2]oct-3-yl ester 9H-fluoren-9-yl ester

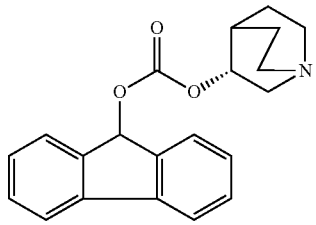 [SMILES: O=C(OC1c2ccccc2-c2ccccc21)O[C@H]1CN2CCC1CC2]

The desired product was prepared by reacting imidazole-1-carboxylic acid (R)-1-aza-bicyclo[2.2.2]oct-3-yl ester with fluorenol.

$^1$H NMR analysis (300 MHz, DMSO-d6)
δ: 7.86 (d, 2H, J=7.5 Hz), 7.63 (t, 2H, J=6.5 Hz), 7.48 (t, 2H, J=7.5 Hz), 7.36 (m, 2H), 6.60 (s, 1H), 4.77 (t, 1H, J=4.2 Hz), 3.19 (dd, 1H, J=8.3, 14.9 Hz), 2.65 (m, 5H), 2.04 (d, 1H, J=2.9 Hz), 1.55 (m, 4H).

Example 5

Carbonic acid (R)-1-aza-bicyclo[2.2.2]oct-3-yl ester 3-fluoro-benzyl ester

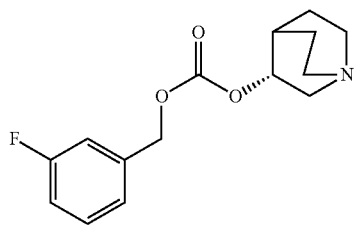 [SMILES: O=C(OCc1cccc(F)c1)O[C@H]1CN2CCC1CC2]

The desired product was prepared by reacting imidazole-1-carboxylic acid (R)-1-aza-bicyclo[2.2.2]oct-3-yl ester with 3-fluoro-benzol.

$^1$H NMR analysis (300 MHz, DMSO-d6)
δ: 7.43 (m, 1H), 7.18 (m, 3H), 5.15 (s, 2H), 4.66 (m, 1H), 3.11 (m, 1H), 2.54 (m, 4H), 1.96 (m, 1H), 1.49 (m, 5H).

Example 6

Carbonic acid (R)-1-aza-bicyclo[2.2.2]oct-3-yl ester 4-fluoro-benzyl ester

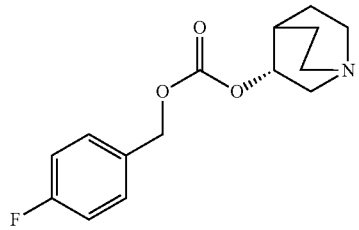 [SMILES: O=C(OCc1ccc(F)cc1)O[C@H]1CN2CCC1CC2]

The desired product was prepared by reacting imidazole-1-carboxylic acid (R)-1-aza-bicyclo[2.2.2]oct-3-yl ester with 4-fluoro-benzol.

$^1$H NMR analysis (300 MHz, DMSO-d6)
δ: 7.46 (m, 2H), 7.22 (m, 2H), 5.11 (s, 2H), 4.63 (m, 1H), 2.61 (m, 5H), 1.95 (d, 1H, J=3.0 Hz), 1.48 (m, 5H).

Example 7

Carbonic acid (R)-1-aza-bicyclo[2.2.2]oct-3-yl ester 4-bromo-benzyl ester

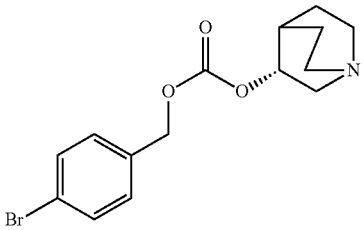 [SMILES: O=C(OCc1ccc(Br)cc1)O[C@H]1CN2CCC1CC2]

The desired product was prepared by reacting imidazole-1-carboxylic acid (R)-1-aza-bicyclo[2.2.2]oct-3-yl ester with 4-bromo-benzol.

Example 8

Carbonic acid (R)-1-aza-bicyclo[2.2.2]oct-3-yl ester biphenyl-2-yl ester

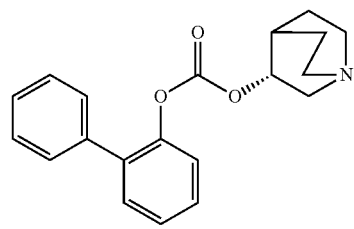 [SMILES: O=C(Oc1ccccc1-c1ccccc1)O[C@H]1CN2CCC1CC2]

The desired product was prepared by reacting imidazole-1-carboxylic acid (R)-1-aza-bicyclo[2.2.2]oct-3-yl ester with 2-hydroxy biphenyl.

Example 9

Carbonic acid (R)-1-aza-bicyclo[2.2.2]oct-3-yl ester thiophen-2-ylmethyl ester

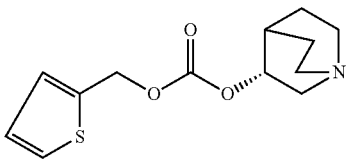 [SMILES: O=C(OCc1cccs1)O[C@H]1CN2CCC1CC2]

The desired product was prepared by reacting imidazole-1-carboxylic acid (R)-1-aza-bicyclo[2.2.2]oct-3-yl ester with 2-hydroxy methyl thiophene.
$^1$H NMR analysis (300 MHz, DMSO-d6)
δ: 7.62 (m, 1H), 7.24 (m, 1H), 7.07 (M, 1H), 5.33 (s, 2H), 4.67 (m, 1H), 3.14 (m, 1H), 2.64 (m, 5H), 1.98 (d, 1H, J=3.1 Hz), 1.30 (m, 4H).

Example 10

Carbonic acid (R)-1-aza-bicyclo[2.2.2]oct-3-yl ester bis-(4-chloro-phenyl)-methyl ester

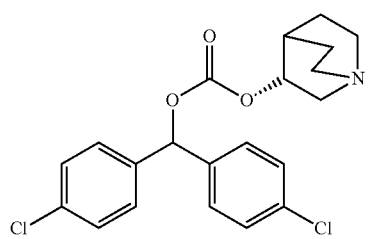

The desired product was prepared by reacting imidazole-1-carboxylic acid (R)-1-aza-bicyclo[2.2.2]oct-3-yl ester with bis-(4-chloro-phenol).
$^1$H NMR analysis (300 MHz, DMSO-d6)
δ: 7.47 (m, 8H), 6.74 (s, 1H), 4.66 (t, 1H, J=4.0 Hz), 3.13 (m, 1H), 2.66 (m, 5H), 1.97 (d, 1H, J=3.0 Hz), 1.51 (m, 4H).

Example 11

Carbonic acid (R)-1-aza-bicyclo[2.2.2]oct-3-yl ester bis-(4-bromo-phenyl)-methyl ester

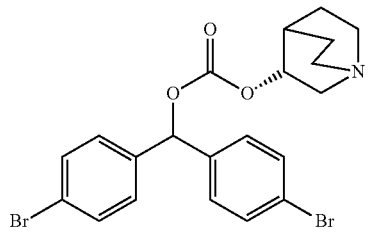

The desired product was prepared by reacting imidazole-1-carboxylic acid (R)-1-aza-bicyclo[2.2.2]oct-3-yl ester with bis-(4-bromo-phenol).
$^1$H NMR analysis (300 MHz, DMSO-d6)
δ: 7.59 (m, 4H), 7.37 (m, 4H), 6.68 (s, 1H), 4.63 (t, 1H, J=3.0 Hz), 3.30 (s, 1 J), 3.08 (m, 1H), 2.64 (m, 4H), 1.94 (d, 1H, J=3.0 Hz), 1.59 (m, 4H)

Example 12

Carbonic acid (R)-1-aza-bicyclo[2.2.2]oct-3-yl ester bis-(4-fluoro-phenyl)-methyl ester

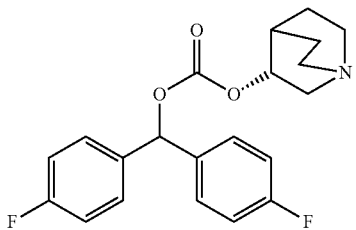

The desired product was prepared by reacting imidazole-1-carboxylic acid (R)-1-aza-bicyclo[2.2.2]oct-3-yl ester with bis-(4-fluoro-phenol).
$^1$H NMR analysis (300 MHz, CDCl$_3$-d6)
δ: 7.34 (m, 4H), 7.06 (m, 4H), 6.67 (s, 1H), 4.72 (m, 1H), 3.23 (m, 1H), 2.83 (m, 5H), 2.08 (m, 1H), 1.49 (m, 4H).

Example 13

Carbonic acid (R)-1-aza-bicyclo[2.2.2]oct-3-yl ester 3-bromo-benzyl ester

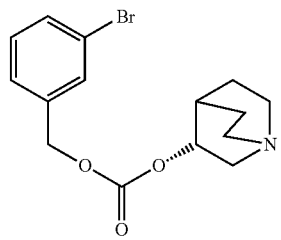

The desired product was prepared by reacting imidazole-1-carboxylic acid (R)-1-aza-bicyclo[2.2.2]oct-3-yl ester with 3-bromo-benzol.

Example 14

Preparation of (R)-3-[Bis-(3-fluoro-phenyl)-methoxycarbonyloxy]-1-(2-oxo-2-thiophen-2-yl-ethyl)-1-azonia-bicyclo[2.2.2]octane; chloride (compound 1)

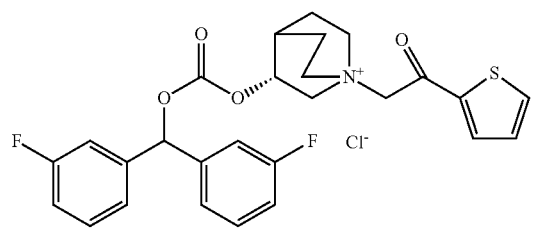 [SMILES: O=C(OC(c1cccc(F)c1)c1cccc(F)c1)O[C@H]1C[N+]2(CC(=O)c3cccs3)CCC1CC2 ; [Cl-]]

The desired product was prepared by reacting 1.4 g, (3.7 mmol) of carbonic acid (R)-1-aza-bicyclo[2.2.2]oct-3-yl ester bis-(3-fluoro-phenyl)-methyl ester (obtained as described in example 2) with 2-(2-chloro)acetylthiophene (602 mg, 3.7 mmol) in EtOAc (5 ml). After stirring for 8 hours at room temperature, the solid precipitated was filtered, washed with Et$_2$O (2 ml) and dried under vacuum at 50° C. 1.3 g of the title compound was obtained as white solid.

$^1$H NMR analysis (300 MHz, DMSO-d6)

δ: 2.06-1.97 (4H, m), 2.42 (1H, br s), 3.86-3.71 (6H, m), 4.25 (1H, m), 5.13 (2H, s), 6.78 (1H, s), 7.47-7.15 (9H, m), 8.11 (1H, d), 8.22 (1H, d).

The following compounds were prepared using the route described in Example 14 and in particular by reacting the compounds described in Examples 3 to 13 with 2-(2-chloro)acetylthiophene, 1-phenethyl bromide, 1-benzyl chloride, methyl iodide, or 1-(3-phenoxy-propyl)bromide, as described in the following.

Example 15

(R)-3-Benzhydryloxycarbonyloxy-1-(2-oxo-2-thiophen-2-yl-ethyl)-1-azonia-bicyclo[2.2.2]octane; chloride (compound 2)

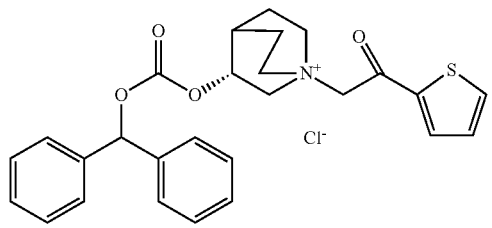 [SMILES: O=C(OC(c1ccccc1)c1ccccc1)O[C@H]1C[N+]2(CC(=O)c3cccs3)CCC1CC2 ; [Cl-]]

The desired product was prepared by reacting carbonic acid (R)-1-aza-bicyclo[2.2.2]oct-3-yl ester benzhydryl ester with 2-(2-chloro)acetylthiophene.

$^1$H NMR analysis (300 MHz, DMSO-d6)

δ: 2.03-1.95 (4H, m), 2.40 (1H, s), 3.88-3.65 (5H, m), 4.19 (1H, m), 5.13 (1H, br s), 5.24 (2H, s), 6.74 (1H, s), 7.45-7.30 (11H, m), 8.16 (1H, d), 8.22 (1H, d).

Example 16

(R)-3-(9H-Fluoren-9-yloxycarbonyloxy)-1-(2-oxo-2-thiophen-2-yl-ethyl)-1-azonia-bicyclo[2.2.2]octane; chloride (compound 3)

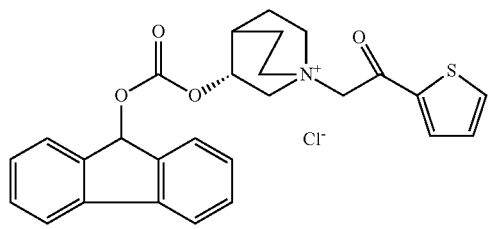

The desired product was prepared by reacting carbonic acid (R)-1-aza-bicyclo[2.2.2]oct-3-yl ester 9H-fluoren-9-yl ester with 2-(2-chloro)acetylthiophene.

$^1$H NMR analysis (300 MHz, DMSO-d6)

δ: 2.09-1.98 (4H, m), 2.50 (1H, s), 3.78-3.69 (4H, m), 3.95 (1H, d), 4.28 (1H, m), 5.27-5.22 (3H, br s), 6.52 (1H, s), 7.39-7.35 (3H, m), 7.50 (2H, d), 7.67 (2H, t), 8.17 (1H, d), 8.23 (1H, d).

Example 17

(R)-3-(3-Fluoro-benzyloxycarbonyloxy)-1-(2-oxo-2-thiophen-2-yl-ethyl)-1-azonia-bicyclo[2.2.2]octane; chloride (compound 4)

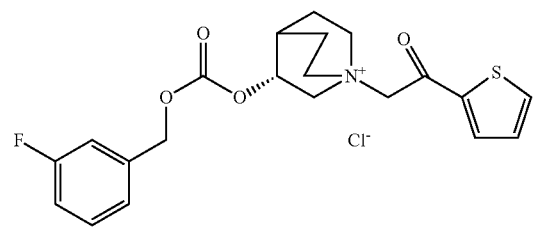 [SMILES: O=C(OCc1cccc(F)c1)O[C@H]1C[N+]2(CC(=O)c3cccs3)CCC1CC2 ; [Cl-]]

The desired product was prepared by reacting carbonic acid (R)-1-aza-bicyclo[2.2.2]oct-3-yl ester 3-fluoro-benzyl ester with 2-(2-chloro)acetylthiophene.

$^1$H NMR analysis (300 MHz, DMSO-d6)

δ: 2.07-1.93 (4H, m), 2.42 (1H, s), 3.93-3.66 (5H, m), 4.27-4.21 (1H, m), 5.14 (1H, s), 5.22 (2H, s), 5.30 (2H, s), 7.50-7.18 (5H, m), 8.21 (2H, m).

Example 18

(R)-3-(4-Fluoro-benzyloxycarbonyloxy)-1-(2-oxo-2-thiophen-2-yl-ethyl)-1-azonia-bicyclo[2.2.2]octane; chloride (compound 5)

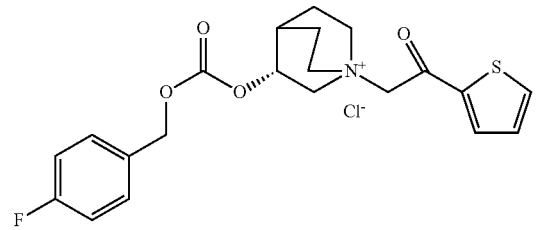 [SMILES: O=C(OCc1ccc(F)cc1)O[C@H]1C[N+]2(CC(=O)c3cccs3)CCC1CC2 ; [Cl-]]

The desired product was prepared by reacting carbonic acid (R)-1-aza-bicyclo[2.2.2]oct-3-yl ester 4-fluoro-benzyl ester with 2-(2-chloro)acetylthiophene.

$^1$H NMR analysis (300 MHz, DMSO-d6)

δ: 2.09-1.89 (4H, m), 2.41 (1H, br s), 3.89-3.67 (5H, m), 4.25-4.18 (1H, m), 5.13 (1H, br s), 5.18 (2H, s), 5.25 (2H, s), 7.24 (2H, t), 7.35 (1H, t), 7.52-7.47 (2H, m), 8.17 (1H, d), 8.22 (1H, d).

Example 19

(R)-3-(4-Bromo-benzyloxycarbonyloxy)-1-(2-oxo-2-thiophen-2-yl-ethyl)-1-azonia-bicyclo[2.2.2]octane; chloride (compound 6)

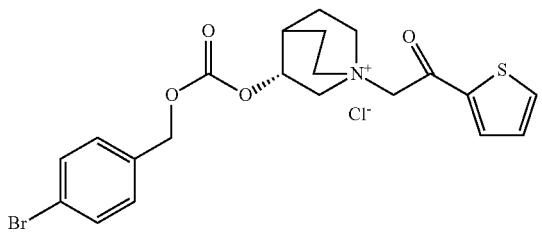 [SMILES: O=C(OCc1ccc(Br)cc1)O[C@H]1C[N+]2(CC(=O)c3cccs3)CCC1CC2 ; [Cl-]]

The desired product was prepared by reacting carbonic acid (R)-1-aza-bicyclo[2.2.2]oct-3-yl ester 4-bromo-benzyl ester with 2-(2-chloro)acetylthiophene.

¹H NMR analysis (300 MHz, DMSO-d6)

δ: 2.06-1.93 (4H, m), 2.41 (1H, s), 3.91-3.35 (5H, m), 4.26-4.19 (1H, m), 5.12 (1H, s), 5.17 (2H, s), 5.27 (2H, s), 7.41-7.34 (3H, m), 7.61 (2H, d), 8.17 (1H, d), 8.22 (1H, d).

Example 20

(R)-3-(Biphenyl-2-yloxycarbonyloxy)-1-(2-oxo-2-thiophen-2-yl-ethyl)-1-azonia-bicyclo[2.2.2]octane; chloride (compound 7)

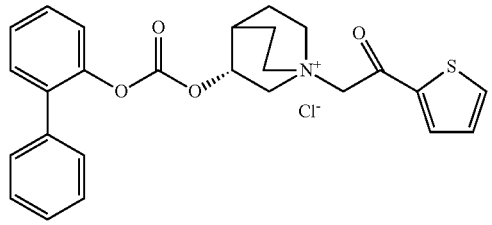 [SMILES: O=C(Oc1ccccc1-c1ccccc1)O[C@H]1C[N+]2(CC(=O)c3cccs3)CCC1CC2 ; [Cl-]]

The desired product was prepared by reacting carbonic acid (R)-1-aza-bicyclo[2.2.2]oct-3-yl ester biphenyl-2-yl ester with 2-(2-chloro)acetylthiophene.

¹H NMR analysis (300 MHz, DMSO-d6)

δ: 2.03-1.88 (4H, m), 2.23 (1H, s), 3.79-3.60 (5H, m), 4.17-4.10 (1H, m), 5.09 (1H, br s), 5.16 (2H, s), 7.49-7.36 (10H, m), 8.14 (1H, d), 8.23 (1H, d).

Example 21

(R)-3-(9H-Fluoren-9-yloxycarbonyloxy)-1-phenethyl-1-azonia-bicyclo[2.2.2]octane; bromide (compound 8)

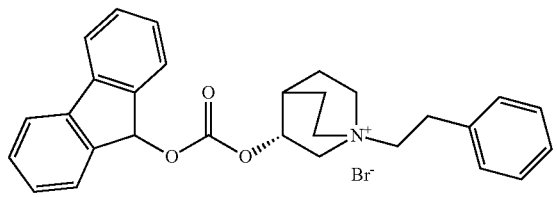 [SMILES: O=C(OC1c2ccccc2-c2ccccc21)O[C@H]1C[N+]2(CCc3ccccc3)CCC1CC2 ; [Br-]]

The desired product was prepared by reacting carbonic acid (R)-1-aza-bicyclo[2.2.2]oct-3-yl ester 9H-fluoren-9-yl ester with 1-phenethyl bromide.

¹H NMR analysis (300 MHz, DMSO-d6)

δ: 2.04-1.92 (4H, m), 2.50 (2H, s), 3.09-3.00 (2H, m), 3.70-3.43 (7H, m), 4.06-3.99 (1H, m), 5.22 (1H, s), 6.65 (1H, s), 7.89-7.26 (13H, m).

Example 22

(R)-1-Benzyl-3-(9H-fluoren-9-yloxycarbonyloxy)-1-azonia-bicyclo[2.2.2]octane; chloride (compound 9)

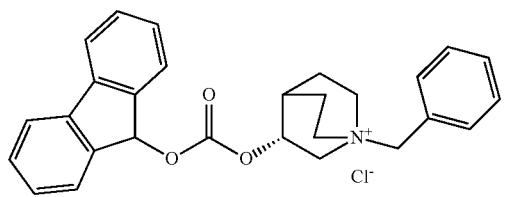 [SMILES: O=C(OC1c2ccccc2-c2ccccc21)O[C@H]1C[N+]2(Cc3ccccc3)CCC1CC2 ; [Cl-]]

The desired product was prepared by reacting carbonic acid (R)-1-aza-bicyclo[2.2.2]oct-3-yl ester 9H-fluoren-9-yl ester with 1-benzyl chloride.

¹H NMR analysis (300 MHz, DMSO-d6)

δ: 1.99-1.81 (4H, m), 2.42 (1H, s), 3.51-3.41 (4H, m), 3.71 (1H, m), 3.92 (1H, m), 4.63 (2H, q), 5.16 (1H, s), 6.64 (1H, s), 7.68-7.36 (11H, m), 7.87 (2H, d).

Example 23

(R)-3-(9H-Fluoren-9-yloxycarbonyloxy)-1-methyl-1-azonia-bicyclo[2.2.2]octane; iodide (compound 10)

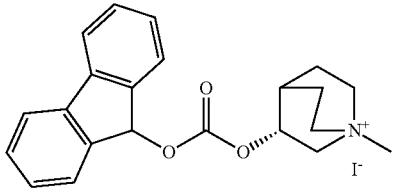 [SMILES: C[N+]12CCC(CC1)[C@@H](OC(=O)OC1c3ccccc3-c3ccccc31)C2 ; [I-]]

The desired product was prepared by reacting carbonic acid (R)-1-aza-bicyclo[2.2.2]oct-3-yl ester 9H-fluoren-9-yl ester with methyl iodide.

¹H NMR analysis (300 MHz, DMSO-d6)

δ: 1.99 (5H, m), 2.50 (1H, s), 3.00 (3H, s), 3.44 (3H, m), 3.47 (1H, d), 3.67 (1H, m), 5.25 (1H, m), 6.64 (1H, s), 7.88-7.36 (8H, m).

Example 24

(R)-3-(9H-Fluoren-9-yloxycarbonyloxy)-1-(3-phenoxy-propyl)-1-azonia-bicyclo[2.2.2]octane; bromide (compound 11)

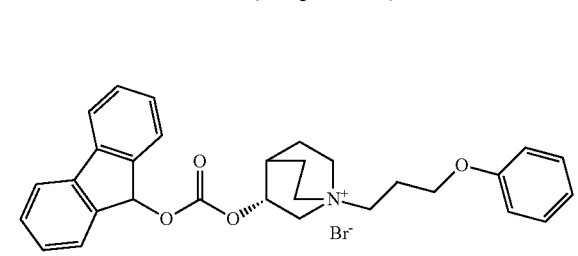

The desired product was prepared by reacting carbonic acid (R)-1-aza-bicyclo[2.2.2]oct-3-yl ester 9H-fluoren-9-yl ester with 1-(3-phenoxy-propyl)bromide.

¹H NMR analysis (300 MHz, DMSO-d6)

δ: 2.19-1.90 (7H, m), 2.50 (1H, s), 3.68-3.32 (6H, m), 4.05-3.96 (3H, m), 5.18 (1H, s), 6.62 (1H, s), 7.88-6.94 (13H, m).

Example 25

(R)-3-(Biphenyl-2-yloxycarbonyloxy)-1-(3-phenoxy-propyl)-1-azonia-bicyclo[2.2.2]octane; bromide (compound 12)

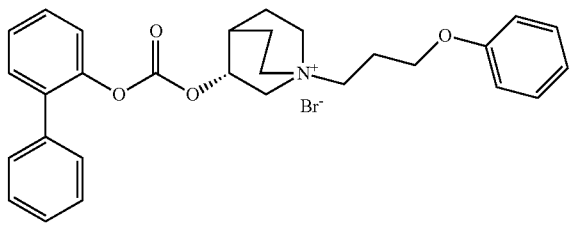 [SMILES: O=C(Oc1ccccc1-c1ccccc1)O[C@H]1C[N+]2(CCCOc3ccccc3)CCC1CC2 ; [Br-]]

The desired product was prepared by reacting carbonic acid (R)-1-aza-bicyclo[2.2.2]oct-3-yl ester biphenyl-2-yl ester with 1-(3-phenoxy-propyl)bromide.

¹H NMR analysis (300 MHz, DMSO-d6)

δ: 2.20-1.83 (7H, m), 2.50 (2H, s), 3.55-3.28 (5I-1, m), 3.90-3.83 (1H, m), 4.05 (2H, t), 4.98 (1H, br s), 6.99-6.95 (3H, m), 7.50-7.30 (11H, m).

Example 26

(R)-3-(Biphenyl-2-yloxycarbonyloxy)-1-methyl-1-azonia-bicyclo[2.2.2]octane; iodide (compound 13)

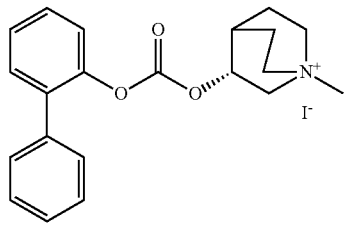 [SMILES: C[N+]12CCC(CC1)[C@@H](OC(=O)Oc1ccccc1-c1ccccc1)C2 ; [I-]]

The desired product was prepared by reacting carbonic acid (R)-1-aza-bicyclo[2.2.2]oct-3-yl ester biphenyl-2-yl ester with methyl iodide.

¹H NMR analysis (300 MHz, DMSO-d6)

δ: 2.18-1.80 (6H, m), 2.95 (3H, s), 3.47-3.32 (4H, m), 3.84-3.75 (1H, m), 4.98-4.96 (1H, m), 5.52-7.39 (9H, m).

Example 27

(R)-1-(2-Oxo-2-thiophen-2-yl-ethyl)-3-(thiophen-2-ylmethoxycarbonyloxy)-1-azonia-bicyclo[2.2.2]octane; chloride (compound 14)

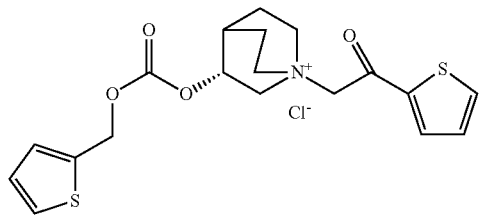 [SMILES: O=C(OCc1cccs1)O[C@H]1C[N+]2(CC(=O)c3cccs3)CCC1CC2 ; [Cl-]]

The desired product was prepared by reacting carbonic acid (R)-1-aza-bicyclo[2.2.2]oct-3-yl ester thiophen-2-ylmethyl ester with 2-(2-chloro)acetylthiophene.

¹H NMR analysis (300 MHz, DMSO-d6)

δ: 2.10-1.95 (4H, m), 2.44 (1H, br s), 3.87-3.66 (5H, m), 4.25-4.16 (1H, m), 5.16 (3H, s), 5.40 (2H, s), 7.66-7.08 (4H, m), 8.15 (1H, dd), 8.24 (1H, dd).

Example 28

(R)-3-[Bis-(4-chloro-phenyl)-methoxycarbonyloxy]-1-(2-oxo-2-thiophen-2-yl-ethyl)-1-azonia-bicyclo[2.2.2]octane; chloride (compound 15)

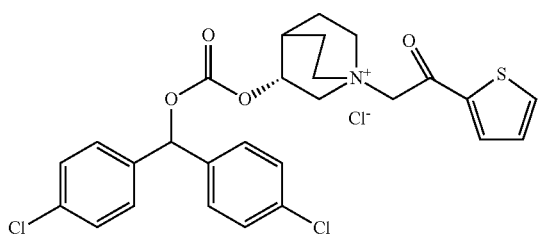 [SMILES: O=C(OC(c1ccc(Cl)cc1)c1ccc(Cl)cc1)O[C@H]1C[N+]2(CC(=O)c3cccs3)CCC1CC2 ; [Cl-]]

The desired product was prepared by reacting carbonic acid (R)-1-aza-bicyclo[2.2.2]oct-3-yl ester bis-(4-chlorophenyl)-methyl ester with 2-(2-chloro)acetylthiophene.

¹H NMR analysis (300 MHz, DMSO-d6)

δ: 1.90-2.06 (4H, m), 2.41 (1H, s), 3.61-3.85 (5H, m), 4.14 (1H, s), 5.12 (3H, s), 7.35 (1H, t), 7.47 (9H, d), 8.11 (1H, d), 8.22 (1H, d).

Example 29

(R)-3-[Bis-(4-bromo-phenyl)-methoxycarbonyloxy]-1-(2-oxo-2-thiophen-2-yl-ethyl)-1-azonia-bicyclo[2.2.2]octane; chloride (compound 16)

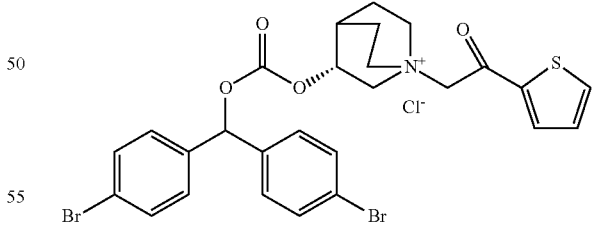

The desired product was prepared by reacting carbonic acid (R)-1-aza-bicyclo[2.2.2]oct-3-yl ester bis-(4-bromophenyl)-methyl ester with 2-(2-chloro)acetylthiophene.

¹H NMR analysis (300 MHz, DMSO-d6)

δ: 2.09-1.96 (4H, m), 2.40 (1H, s), 3.78-3.72 (5H, m), 3.86-3.82 (1H, m), 5.16-5.13 (3H, m), 6.75 (1H, s), 7.43-7.35 (5H, m), 7.63-7.59 (4H, m), 8.12 (1H, d), 8.22 (1H, d).

Example 30

(R)-3-[Bis-(4-fluoro-phenyl)-methoxycarbonyloxy]-1-(2-oxo-2-thiophen-2-yl-ethyl)-1-azonia-bicyclo[2.2.2]octane; chloride (compound 17)

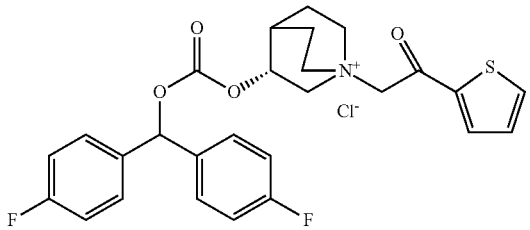 [SMILES: O=C(OC(c1ccc(F)cc1)c1ccc(F)cc1)O[C@H]1C[N+]2(CC(=O)c3cccs3)CCC1CC2 ; [Cl-]]

The desired product was prepared by reacting carbonic acid (R)-1-aza-bicyclo[2.2.2]oct-3-yl ester bis-(4-fluoro-phenyl)-methyl ester with 2-(2-chloro)acetylthiophene.

$^1$H NMR analysis (300 MHz, DMSO-d6)

δ: 2.09-1.96 (4H, m), 2.40 (1H, br s), 3.89-3.65 (5H, m), 4.23-4.16 (1H, m), 5.14 (1H, d), 5.23 (2H, d), 6.79 (1H, s), 7.52-7.20 (9H, m), 8.16 (1H, d), 8.22 (1H, d).

Example 31

(R)-3-(3-Bromo-benzyloxycarbonyloxy)-1-(2-oxo-2-thiophen-2-yl-ethyl)-1-azonia-bicyclo[2.2.2]octane; chloride (compound 18)

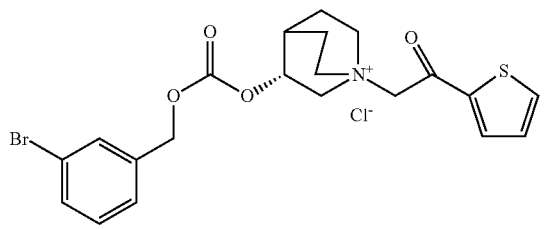 [SMILES: O=C(OCc1cccc(Br)c1)O[C@H]1C[N+]2(CC(=O)c3cccs3)CCC1CC2 ; [Cl-]]

The desired product was prepared by reacting carbonic acid (R)-1-aza-bicyclo[2.2.2]oct-3-yl ester 3-bromo-benzyl ester with 2-(2-chloro)acetylthiophene.

$^1$H NMR analysis (300 MHz, DMSO-d6)

δ: 2.14-1.96 (4H, m), 2.45 (1H, br s), 3.91-3.64 (5H, m), 4.26-4.19 (1H, m), 5.23-5.16 (5H, m), 7.59-7.37 (3H, m), 7.67-7.60 (2H, m), 8.17 (1H, d), 8.25 (1H, d).

Example 32

Preparation of carbonic acid (R)-(1-aza-bicyclo[2.2.2]oct-3-yl)ester (3-fluoro-phenyl)-(2-fluoro-phenyl)-methyl ester

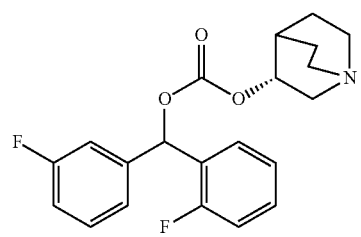 [SMILES: O=C(OC(c1cccc(F)c1)c1ccccc1F)O[C@H]1CN2CCC1CC2]

NaH (60% dispersion in mineral oil, 36.3 mg, 0.9 mmol) was added to a solution of (2-fluoro-phenyl)-(3-fluoro-phenyl)-methanol (200 mg, 0.9 mmol) in anhydrous THF (3 ml), at 0° C. The reaction mixture was stirred at this temperature for 30 minutes, then (R)-quinuclidin-3-yl 1H-imidazole-1-carboxylate (201 mg, 0.9 mmol), obtained as described in Example 1, was added and the stirring continued at room temperature for 1 hour. Then a saturated solution of NH$_4$Cl was added, and the aqueous phase was extracted with EtOAc (3×30 ml). The organic phase was dried over anhydrous sodium sulfate, and the solvent was evaporated under reduced pressure. The resulting crude was purified by flash chromatography on silica gel eluting with EtOAc/MeOH=9/1. The desired product was collected as colorless viscous oil (244 mg; 72% yield; mixture of diasteroisomers).

$^1$H NMR analysis (300 MHz, DMSO-d$_6$)

δ: 7.34-7.57 (m, 3H), 7.11-7.33 (m, 5H), 6.87 (s, 1H), 4.50-4.81 (m, 1H), 3.13 (dd, 1H), 2.53-2.81 (m, 5H), 1.91-2.08 (m, 1H), 1.54-1.76 (m, 2H), 1.41-1.54 (m, 1H), 1.26-1.41 (m, 1H).

LC-MS (ESI POS): 374.14 (MH+).

The following intermediates (example 33 to 42) were obtained with a process similar to the one used to prepare the compound of Example 32, by reacting the compound prepared in Example 1 with the suitable alcohols, such as bis(2-chlorophenyl)methanol, phenyl-o-tolyl-methanol, (3-fluoro-phenyl)-(3-methoxy-phenyl)-methanol, cyclohexyl-(3-fluoro-phenyl)-methanol, (3-chloro-phenyl)-(3-fluoro-phenyl)-methanol, (3,5-difluoro-phenyl)-(3-fluoro-phenyl)-methanol, (3-fluoro-phenyl)-m-tolyl-methanol, (3-fluoro-phenyl)-(4-methylsulfanyl-phenyl)-methanol, (3-fluoro-phenyl)-(4-fluoro-phenyl)-methanol, (3,4-difluoro-phenyl)-phenyl-methanol, and (3-fluoro-phenyl)-phenyl-methanol.

Example 33

Carbonic acid (R)-(1-aza-bicyclo[2.2.2]oct-3-yl)ester bis-(2-chloro-phenyl)-methyl ester

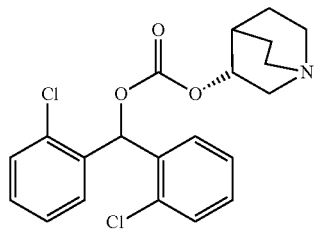

The desired product was prepared by reacting imidazole-1-carboxylic acid (R)-1-aza-bicyclo[2.2.2]oct-3-yl ester with bis(2-chlorophenyl)methanol.

$^1$H NMR analysis (300 MHz, DMSO-d$_6$)

δ: 7.51-7.63 (m, 2H), 7.37-7.51 (m, 4H), 7.22-7.31 (m, 2H), 7.21 (s, 1H), 4.53-4.77 (m, 1H), 3.13 (dd, 1H), 2.54-2.81 (m, 5H), 1.88-2.04 (m, 1H), 1.54-1.78 (m, 2H), 1.41-1.54 (m, 1H), 1.27-1.41 (m, 1H).

LC-MS (ESI POS): 406.05 (MH+).

Example 34

Carbonic acid (R)-(1-aza-bicyclo[2.2.2]oct-3-yl)ester phenyl-o-tolyl-methyl ester

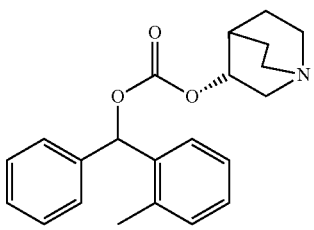

The desired product was prepared by reacting imidazole-1-carboxylic acid (R)-1-aza-bicyclo[2.2.2]oct-3-yl ester with phenyl-o-tolyl-methanol.

$^1$H NMR analysis (300 MHz, DMSO-$d_6$)

δ: 7.09-7.51 (m, 9H), 6.80 (s, 1H), 4.47-4.79 (m, 1H), 3.10 (dd, 1H), 2.54-2.77 (m, 5H), 2.27 (s, 3H), 1.94 (br. s., 1H), 1.52-1.76 (m, 2H), 1.38-1.52 (m, 1H), 1.16-1.38 (m, 1H).

LC-MS (ESI POS): 352.13 (MH+).

Example 35

Carbonic acid (R)-(1-aza-bicyclo[2.2.2]oct-3-yl)ester (3-fluoro-phenyl)-(3-methoxy-phenyl)-methyl ester

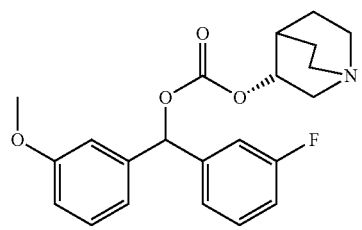

The desired product was prepared by reacting imidazole-1-carboxylic acid (R)-1-aza-bicyclo[2.2.2]oct-3-yl ester with (3-fluoro-phenyl)-(3-methoxy-phenyl)-methanol.

$^1$H NMR analysis (300 MHz, DMSO-$d_6$)

δ: 7.37-7.51 (m, 1H), 7.21-7.35 (m, 3H), 7.08-7.20 (m, 1H), 6.94-7.04 (m, 2H), 6.82-6.92 (m, 1H), 6.65 (s, 1H), 4.53-4.79 (m, 1H), 3.75 (s, 3H), 3.11 (dd, 1H), 2.54-2.79 (m, 5H), 1.86-2.01 (m, 1H), 1.53-1.76 (m, 2H), 1.40-1.53 (m, 1H), 1.21-1.40 (m, 1H).

LC-MS (ESI POS): 386.05 (MH+).

Example 36

Carbonic acid (R)-(1-aza-bicyclo[2.2.2]oct-3-yl)ester cyclohexyl-(3-fluoro-phenyl)-methyl ester

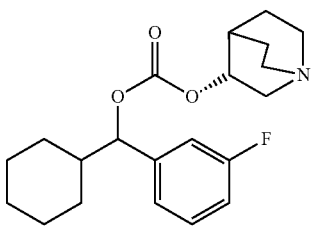

The desired product was prepared by reacting imidazole-1-carboxylic acid (R)-1-aza-bicyclo[2.2.2]oct-3-yl ester with cyclohexyl-(3-fluoro-phenyl)-methanol.

$^1$H NMR analysis (300 MHz, DMSO-$d_6$)

δ: 7.33-7.49 (m, 1H), 7.02-7.21 (m, 3H), 5.31 (d, 1H), 4.34-4.69 (m, 1H), 299-3.21 (m, 1H), 2.43-2.79 (m, 4H), 1.85-1.98 (m, 1H), 0.83-1.83 (m, 16H).

LC-MS (ESI POS): 362.16 (MH+).

Example 37

Carbonic acid (R)-(1-aza-bicyclo[2.2.2]oct-3-yl)ester (3-chloro-phenyl)-(3-fluoro-phenyl)-methyl ester

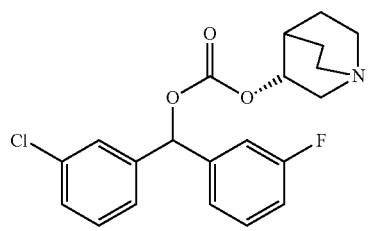

The desired product was prepared by reacting imidazole-1-carboxylic acid (R)-1-aza-bicyclo[2.2.2]oct-3-yl ester with (3-chloro-phenyl)-(3-fluoro-phenyl)-methanol.

$^1$H NMR analysis (300 MHz, DMSO-$d_6$)

δ: 7.50-7.56 (m, 1H) 7.35-7.49 (m, 4H) 7.25-7.35 (m, 2H) 7.08-7.21 (m, 1H), 6.71 (s, 1H) 4.58-4.71 (m, 1H) 3.02-3.17 (m, 1H) 2.54-2.78 (m, 4H) 1.91-1.98 (m, 1H) 1.40-1.70 (m, 3H) 1.21-1.38 (m, 2H).

LC-MS (ESI POS): 390.04 (MH+).

Example 38

Carbonic acid (R)-(1-aza-bicyclo[2.2.2]oct-3-yl)ester (3,5-difluoro-phenyl)-(3-fluoro-phenyl)-methyl ester

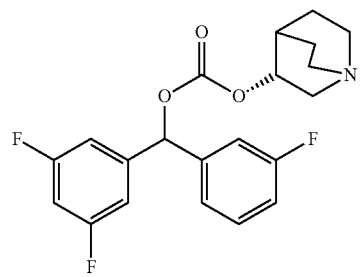

The desired product was prepared by reacting imidazole-1-carboxylic acid (R)-1-aza-bicyclo[2.2.2]oct-3-yl ester with (3,5-difluoro-phenyl)-(3-fluoro-phenyl)-methanol. $^1$H NMR analysis (300 MHz, DMSO-$d_6$)

δ: 7.40-7.60 (m, 2H) 7.10-7.26 (m, 5H) 6.97 (d, 1H) 4.58-4.73 (m, 1H) 3.01-3.19 (m, 1H) 2.54-2.72 (m, 5H) 1.85-2.06 (m, 1H) 1.40-1.69 (m, 3H) 1.23-1.38 (m, 1H).

LC-MS (ESI POS): 392.05 (MH+).

Example 39

Carbonic acid (R)-(1-aza-bicyclo[2.2.2]oct-3-yl)ester (3-fluoro-phenyl)-m-tolyl-methyl ester

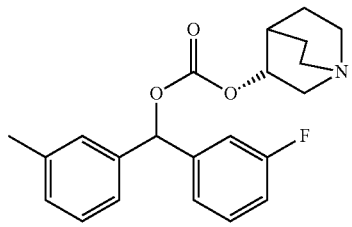

The desired product was prepared by reacting imidazole-1-carboxylic acid (R)-1-aza-bicyclo[2.2.2]oct-3-yl ester with (3-fluoro-phenyl)-m-tolyl-methanol.

¹H NMR analysis (300 MHz, DMSO-$d_6$)
δ: 7.36-7.49 (m, 1H), 7.06-7.32 (m, 7H), 6.64 (s, 1H), 4.32-4.80 (m, 1H), 3.10 (dd, 1H), 2.54-2.77 (m, 5H), 2.30 (s, 3H), 1.87-2.04 (m, 1H), 1.11-1.76 (m, 4H).
LC-MS (ESI POS): 370.1 (MH+).

Example 40

Carbonic acid (R)-(1-aza-bicyclo[2.2.2]oct-3-yl)ester (3-fluoro-phenyl)-(4-methylsulfanyl-phenyl)-methyl ester

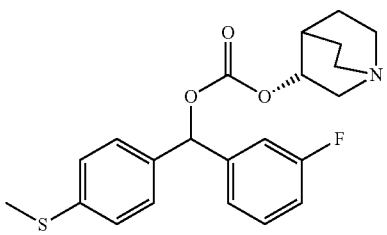

The desired product was prepared by reacting imidazole-1-carboxylic acid (R)-1-aza-bicyclo[2.2.2]oct-3-yl ester with (3-fluoro-phenyl)-(4-methylsulfanyl-phenyl)-methanol.

¹H NMR analysis (300 MHz, DMSO-$d_6$)
δ: 7.31-7.49 (m, 3H), 7.20-7.30 (m, 4H), 7.07-7.20 (m, 1H), 6.66 (s, 1H), 4.64 (ddd, 1H), 3.10 (dd, 1H), 2.54-2.76 (m, 5H), 2.46 (s, 3H), 1.86-2.02 (m, 1H), 1.38-1.77 (m, 3H), 1.16-1.38 (m, 1H).
LC-MS (ESI POS): 401.93 (MH+).

Example 41

Carbonic acid (R)-(1-aza-bicyclo[2.2.2]oct-3-yl)ester (4-fluoro-phenyl)-(3-fluoro-phenyl)-methyl ester

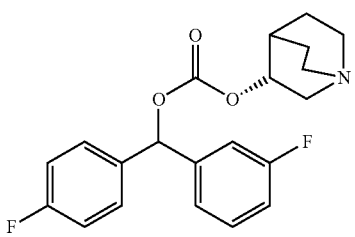

The desired product was prepared by reacting imidazole-1-carboxylic acid (R)-1-aza-bicyclo[2.2.2]oct-3-yl ester with (3-fluoro-phenyl)-(4-fluoro-phenyl)-methanol.

¹H NMR analysis (300 MHz, DMSO-$d_6$)
δ: 7.36-7.56 (m, 3H), 7.03-7.32 (m, 5H), 6.72 (s, 1H), 4.64 (ddd, 1H), 3.10 (dd, 1H), 2.65-2.80 (m, 2H), 2.54-2.65 (m, 3H), 1.95 (br. s., 1H), 1.53-1.74 (m, 2H), 1.40-1.53 (m, 1H), 1.18-1.40 (m, 1H).
LC-MS (ESI POS): 374.14 (MH+).

Example 42

Carbonic acid (R)-(1-aza-bicyclo[2.2.2]oct-3-yl)ester (3,4-difluoro-phenyl)-phenyl-methyl ester

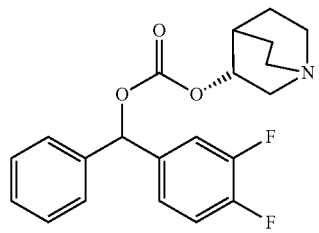

The desired product was prepared by reacting imidazole-1-carboxylic acid (R)-1-aza-bicyclo[2.2.2]oct-3-yl ester with (3,4-difluoro-phenyl)-phenyl-methanol.

¹H NMR analysis (300 MHz, DMSO-$d_6$)
δ: 7.47-7.62 (m, 1H), 7.20-7.47 (m, 7H), 6.69 (s, 1H), 4.64 (m, 1H), 3.10 (dd, 1H), 2.54-2.79 (m, 5H), 1.87-2.01 (m, 1H), 1.53-1.74 (m, 2H), 1.39-1.53 (m, 1H), 1.17-1.39 (m, 1H).
LC-MS (ESI POS): 373.96 (MH+).

Example 43

Carbonic acid (R)-(1-aza-bicyclo[2.2.2]oct-3-yl)ester (3-fluoro-phenyl)-phenyl-methyl ester

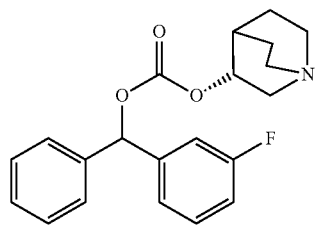

The desired product was prepared by reacting imidazole-1-carboxylic acid (R)-1-aza-bicyclo[2.2.2]oct-3-yl ester with (3-fluoro-phenyl)-phenyl-methanol.

¹H NMR analysis (300 MHz, DMSO-$d_6$)
δ: 7.21-7.55 (m, 7H), 7.00-7.20 (m, 2H), 6.69 (s, 1H), 4.52-4.73 (m, 1H), 3.10 (dd, 1H), 2.54-2.78 (m, 5H), 1.89-1.97 (m, 1H), 1.52-1.75 (m, 2H), 1.40-1.52 (m, 1H), 1.19-1.39 (m, 1H).
LC-MS (ESI POS): 356.16 (MH+).

The following compounds were prepared using the route described in Example 14 and in particular by reacting the compound described in Example 2 with 2-bromo-1-phenyl-ethanone, 2-bromo-acetamide, 2-bromo-1-p-tolyl-ethanone, 2-bromo-1-(4-fluoro-phenyl)-ethanone, 2-bromo-1-(4-methoxy-phenyl)-ethanone, 2-bromo-1-thiophen-3-yl-ethanone, 2-bromo-N-phenyl-acetamide, 2-bromo-1-(5-chloro-thiophen-2-yl)-ethanone, 2-bromo-1-(3,5-dibromo-thiophen-2-yl)-ethanone, 2-bromo-1-thiazol-2-yl-ethanone, 2-bromo-1-o-tolyl-ethanone, 2-bromo-1-m-tolyl-ethanone, 5-bromo-2-methylpent-2-ene, 1-benzo[b]thiophen-2-yl-2-bromo-ethanone, bromomethyl-benzene, (2-bromoethoxy)benzene, or methyl iodide, as described in the following.

Example 44

(R)-3-[Bis-(3-fluoro-phenyl)-methoxycarbonyloxy]-1-(2-oxo-2-phenyl-ethyl)-1-azonia-bicyclo[2.2.2]octane; bromide (compound 19)

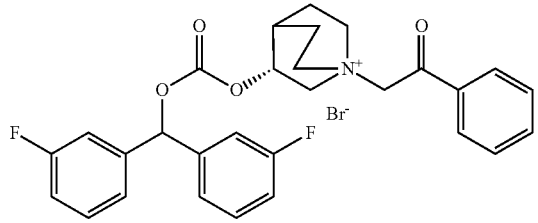 [SMILES: O=C(OC(c1cccc(F)c1)c1cccc(F)c1)O[C@H]1C[N+]2(CC(=O)c3ccccc3)CCC1CC2 ; [Br-]]

The desired product was prepared by reacting (R)-1-azabicyclo[2.2.2]oct-3-yl ester bis-(3-fluoro-phenyl)-methyl ester with 2-bromo-1-phenyl-ethanone.

$^1$H NMR analysis (300 MHz, DMSO-$d_6$)

δ: 7.89-8.06 (m, 2H), 7.70-7.86 (m, 1H), 7.56-7.70 (m, 2H), 7.39-7.55 (m, 2H), 7.26-7.39 (m, 4H), 7.07-7.26 (m, 2H), 6.79 (s, 1H), 5.19 (s, 2H), 5.13-5.18 (m, 1H), 4.03-4.27 (m, 1H), 3.56-3.86 (m, 5H), 2.35-2.47 (m, 1H), 1.91-2.16 (m, 4H).

LC-MS (ESI POS): 492.10 (MH+).

Example 45

(R)-3-[Bis-(3-fluoro-phenyl)-methoxycarbonyloxy]-1-carbamoylmethyl-1-azonia-bicyclo[2.2.2]octane; bromide (compound 20)

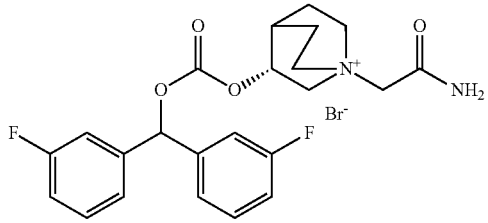 [SMILES: NC(=O)C[N+]12CCC(CC1)[C@@H](OC(=O)OC(c1cccc(F)c1)c1cccc(F)c1)C2 ; [Br-]]

The desired product was prepared by reacting (R)-1-azabicyclo[2.2.2]oct-3-yl ester bis-(3-fluoro-phenyl)-methyl ester with 2-bromo-acetamide.

$^1$H NMR analysis (300 MHz, DMSO-$d_6$)

δ: 7.92 (br. s., 1H), 7.69 (br. s., 1H), 7.38-7.53 (m, 2H), 7.25-7.38 (m, 4H), 7.06-7.25 (m, 2H), 6.77 (s, 1H), 5.10 (br. s., 1H), 4.02-4.20 (m, 1H), 3.99 (s, 2H), 3.76-3.85 (m, 1H), 3.49-3.74 (m, 4H), 2.32-2.43 (m, 1H), 1.83-2.09 (m, 4H).

LC-MS (ESI POS): 431.10 (MH+).

Example 46

(R)-3-[Bis-(3-fluoro-phenyl)-methoxycarbonyloxy]-1-(2-oxo-2-p-tolyl-ethyl)-1-azonia-bicyclo[2.2.2]octane; bromide (compound 21)

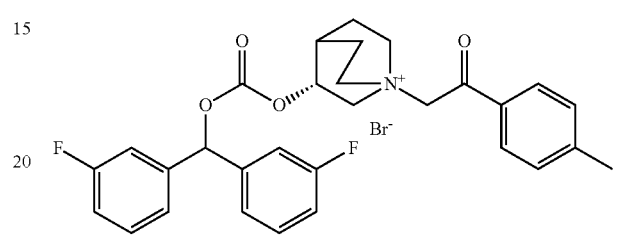

The desired product is prepared by reacting (R)-1-azabicyclo[2.2.2]oct-3-yl ester bis-(3-fluoro-phenyl)-methyl ester with 2-bromo-1-p-tolyl-ethanone.

$^1$H NMR analysis (300 MHz, DMSO-$d_6$)

δ: 7.73-8.03 (m, 2H), 7.26-7.50 (m, 8H), 7.03-7.25 (m, 2H), 6.78 (s, 1H), 5.15-5.21 (m, 1H), 5.14 (s, 2H), 4.07-4.26 (m, 1H), 3.76-3.93 (m, 1H), 3.48-3.76 (m, 4H), 2.43-2.47 (m, 1H), 2.42 (s, 3H), 1.91-2.15 (m, 4H).

LC-MS (ESI POS): 505.95 (MH+).

Example 47

(R)-3-[Bis-(3-fluoro-phenyl)-methoxycarbonyloxy]-1-[2-(4-fluoro-phenyl)-2-oxo-ethyl]-1-azonia-bicyclo[2.2.2]octane; bromide (compound 22)

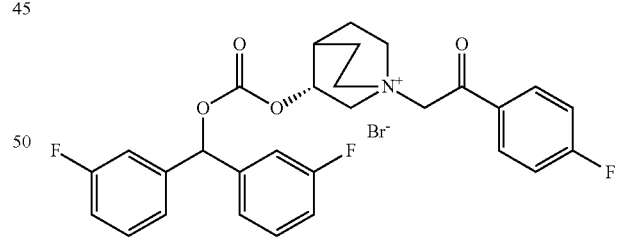

The desired product is prepared by reacting (R)-1-azabicyclo[2.2.2]oct-3-yl ester bis-(3-fluoro-phenyl)-methyl ester with 2-bromo-1-(4-fluoro-phenyl)-ethanone.

$^1$H NMR analysis (300 MHz, DMSO-$d_6$)

δ: 7.98-8.18 (m, 2H), 7.40-7.58 (m, 4H), 7.25-7.40 (m, 4H), 7.05-7.25 (m, 2H), 6.78 (s, 1H), 5.17 (s, 2H), 5.13-5.24 (m, 1H), 4.08-4.27 (m, 1H), 3.55-3.86 (m, 5H), 2.34-2.47 (m, 1H), 1.90-2.17 (m, 4H).

LC-MS (ESI POS): 509.94 (MH+).

Example 48

(R)-3-[Bis-(3-fluoro-phenyl)-methoxycarbonyloxy]-1-[2-(4-methoxy-phenyl)-2-oxo-ethyl]-1-azonia-bicyclo[2.2.2]octane; bromide (compound 23)

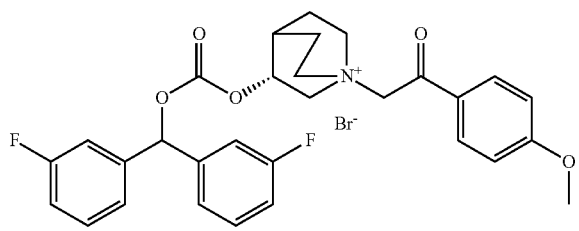 [SMILES: COc1ccc(C(=O)C[N+]23CCC(CC2)[C@@H](OC(=O)OC(c2cccc(F)c2)c2cccc(F)c2)C3)cc1 ; [Br-]]

The desired product was prepared by reacting (R)-1-azabicyclo[2.2.2]oct-3-yl ester bis-(3-fluoro-phenyl)-methyl ester with 2-bromo-1-(4-methoxy-phenyl)-ethanone.

$^1$H NMR analysis (300 MHz, DMSO-d$_6$) δ: 7.92-8.03 (m, 2H), 7.25-7.52 (m, 6H), 6.95-7.25 (m, 4H), 6.78 (s, 1H), 5.13-5.24 (m, 1H), 5.10 (s, 2H), 4.05-4.27 (m, 1H), 3.88 (s, 3H), 3.48-3.87 (m, 5H), 2.33-2.46 (m, 1H), 1.90-2.15 (m, 4H).

LC-MS (ESI POS): 521.98 (MH+).

Example 49

(R)-3-[Bis-(3-fluoro-phenyl)-methoxycarbonyloxy]-1-(2-oxo-2-thiophen-3-yl-ethyl)-1-azonia-bicyclo[2.2.2]octane; bromide (compound 24)

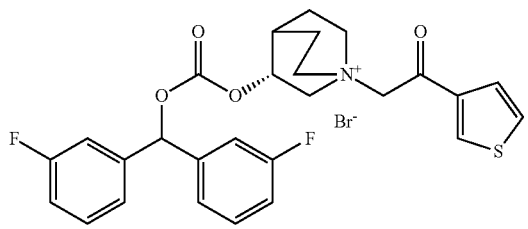 [SMILES: O=C(OC(c1cccc(F)c1)c1cccc(F)c1)O[C@H]1C[N+]2(CC(=O)c3ccsc3)CCC1CC2 ; [Br-]]

The desired product was prepared by reacting (R)-1-azabicyclo[2.2.2]oct-3-yl ester bis-(3-fluoro-phenyl)-methyl ester with 2-bromo-1-thiophen-3-yl-ethanone.

$^1$H NMR analysis (300 MHz, DMSO-d$_6$)

δ: 8.62 (dd, 1H), 7.74 (dd, 1H), 7.56 (dd, 1H), 7.39-7.52 (m, 2H), 7.27-7.39 (m, 4H), 7.09-7.25 (m, 2H), 6.78 (s, 1H), 5.10-5.27 (m, 1H), 5.03 (s, 2H), 4.14 (dd, 1H), 3.45-3.94 (m, 5H), 2.36-2.47 (m, 1H), 1.70-2.19 (m, 4H).

LC-MS (ESI POS): 497.89 (MH+).

Example 50

(R)-3-[Bis-(3-fluoro-phenyl)-methoxycarbonyloxy]-1-phenylcarbamoylmethyl-1-azonia-bicyclo[2.2.2]octane; bromide (compound 25)

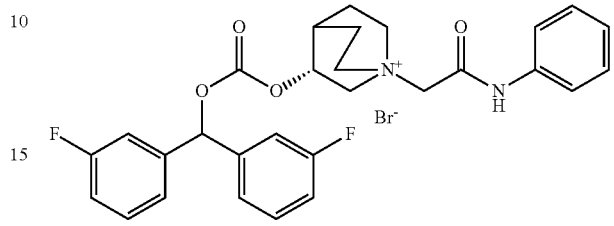

The desired product was prepared by reacting (R)-1-azabicyclo[2.2.2]oct-3-yl ester bis-(3-fluoro-phenyl)-methyl ester with 2-bromo-N-phenyl-acetamide.

$^1$H NMR analysis (300 MHz, DMSO-d$_6$)

δ: 10.52 (s, 1H), 7.52-7.63 (m, 2H), 7.26-7.51 (m, 8H), 7.01-7.23 (m, 3H), 6.78 (s, 1H), 4.91-5.31 (m, 1H), 4.26 (d, 1H), 4.19 (d, 1H), 4.02-4.20 (m, 1H), 3.81-3.95 (m, 1H), 3.51-3.81 (m, 4H), 2.43 (dd, 1H), 1.71-2.17 (m, 4H).

LC-MS (ESI POS): 506.94 (MH+).

Example 51

(R)-3-[Bis-(3-fluoro-phenyl)-methoxycarbonyloxy]-1-[2-(5-chloro-thiophen-2-yl)-2-oxo-ethyl]-1-azonia-bicyclo[2.2.2]octane; bromide (compound 26)

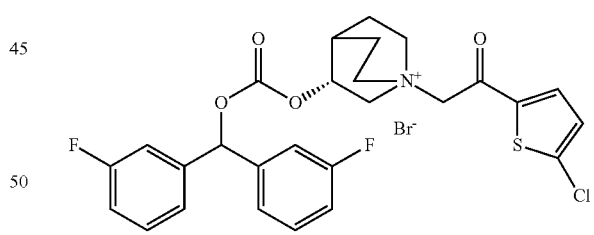

The desired product was prepared by reacting (R)-1-azabicyclo[2.2.2]oct-3-yl ester bis-(3-fluoro-phenyl)-methyl ester with 2-bromo-1-(5-chloro-thiophen-2-yl)-ethanone.

$^1$H NMR analysis (300 MHz, DMSO-d$_6$)

δ: 8.00 (d, 1H), 7.38-7.60 (m, 3H), 7.25-7.38 (m, 4H), 7.02-7.25 (m, 2H), 6.78 (s, 1H), 5.06-5.36 (m, 1H), 4.99 (s, 2H), 3.97-4.24 (m, 1H), 3.51-3.84 (m, 5H), 2.36-2.45 (m, 1H), 1.89-2.15 (m, 4H).

LC-MS (ESI POS): 531.82 (MH+).

Example 52

(R)-3-[Bis-(3-fluoro-phenyl)-methoxycarbonyloxy]-1-[2-(3,5-dibromo-thiophen-2-yl)-2-oxo-ethyl]-1-azonia-bicyclo[2.2.2]octane; chloride (compound 27)

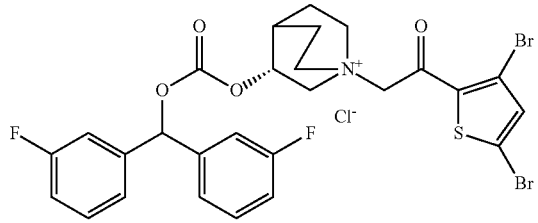 [SMILES: O=C(OC(c1cccc(F)c1)c1cccc(F)c1)O[C@H]1C[N+]2(CC(=O)c3sc(Br)cc3Br)CCC1CC2 ; [Cl-]]

The desired product was prepared by reacting (R)-1-azabicyclo[2.2.2]oct-3-yl ester bis-(3-fluoro-phenyl)-methyl ester with 2-bromo-1-(3,5-dibromo-thiophen-2-yl)-ethanone.

$^1$H NMR analysis (300 MHz, DMSO-$d_6$)

δ: 7.68 (s, 1H), 7.40-7.52 (m, 2H), 7.26-7.39 (m, 4H), 7.11-7.23 (m, 2H), 6.78 (s, 1H), 5.11-5.23 (m, 1H), 5.08 (s, 2H), 4.07-4.32 (m, 1H), 3.49-4.00 (m, 5H), 2.35-2.46 (m, 1H), 1.74-2.19 (m, 4H).

LC-MS (ESI POS): 653.62 (MH+).

Example 53

(R)-3-[Bis-(3-fluoro-phenyl)-methoxycarbonyloxy]-1-(2-oxo-2-thiazol-2-yl-ethyl)-1-azonia-bicyclo[2.2.2]octane; bromide (compound 28)

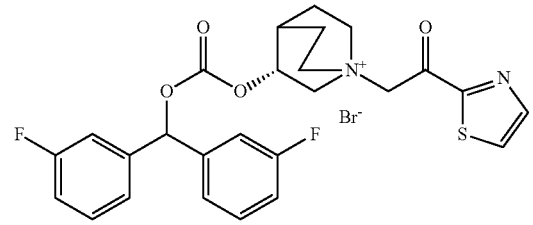 [SMILES: O=C(OC(c1cccc(F)c1)c1cccc(F)c1)O[C@H]1C[N+]2(CC(=O)c3nccs3)CCC1CC2 ; [Br-]]

The desired product was prepared by reacting (R)-1-azabicyclo[2.2.2]oct-3-yl ester bis-(3-fluoro-phenyl)-methyl ester with 2-bromo-1-thiazol-2-yl-ethanone.

$^1$H NMR analysis (300 MHz, DMSO-$d_6$)

δ: 8.39 (d, 1H), 8.24 (d, 1H), 7.39-7.52 (m, 2H), 7.26-7.39 (m, 4H), 7.10-7.25 (m, 2H), 6.78 (s, 1H), 5.22 (s, 2H), 4.98-5.19 (m, 1H), 4.07-4.33 (m, 1H), 3.52-4.01 (m, 5H), 2.36-2.45 (m, 1H), 1.80-2.17 (m, 4H).

LC-MS (ESI POS): 499.04 (MH+).

Example 54

(R)-3-[Bis-(3-fluoro-phenyl)-methoxycarbonyloxy]-1-(2-oxo-2-o-tolyl-ethyl)-1-azonia-bicyclo[2.2.2]octane; bromide (compound 29)

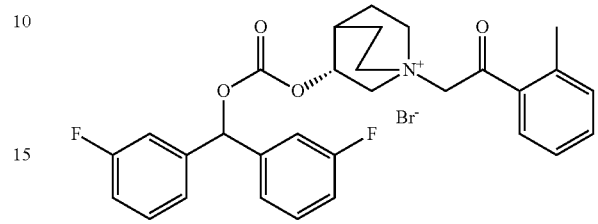

The desired product was prepared by reacting (R)-1-azabicyclo[2.2.2]oct-3-yl ester bis-(3-fluoro-phenyl)-methyl ester with 2-bromo-1-o-tolyl-ethanone.

$^1$H NMR analysis (300 MHz, DMSO-$d_6$)

δ: 7.66-7.92 (m, 1H), 7.52-7.65 (m, 1H), 7.26-7.51 (m, 8H), 7.09-7.24 (m, 2H), 6.79 (s, 1H), 5.11-5.24 (m, 1H), 5.08 (s, 2H), 4.06-4.26 (m, 1H), 3.53-3.92 (m, 5H), 2.46 (s, 3H), 2.36-2.45 (m, 1H), 1.83-2.19 (m, 4H).

LC-MS (ESI POS): 505.95 (MH+).

Example 55

(R)-3-[Bis-(3-fluoro-phenyl)-methoxycarbonyloxy]-1-(2-oxo-2-m-tolyl-ethyl)-1-azonia-bicyclo[2.2.2]octane; bromide (compound 30)

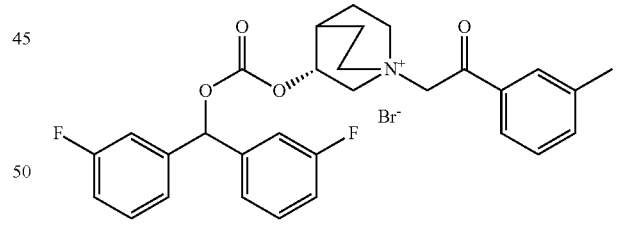

The desired product was prepared by reacting (R)-1-azabicyclo[2.2.2]oct-3-yl ester bis-(3-fluoro-phenyl)-methyl ester with 2-bromo-1-m-tolyl-ethanone.

$^1$H NMR analysis (300 MHz, DMSO-$d_6$)

δ: 7.70-7.84 (m, 2H), 7.39-7.64 (m, 4H), 7.26-7.39 (m, 4H), 7.10-7.24 (m, 2H), 6.79 (s, 1H), 5.17 (s, 2H), 5.15-5.26 (m, 1H), 4.00-4.29 (m, 1H), 3.48-3.90 (m, 5H), 2.42-2.46 (m, 1H), 2.41 (s, 3H), 1.86-2.15 (m, 4H).

LC-MS (ESI POS): 506.11 (MH+).

Example 56

(R)-3-[Bis-(3-fluoro-phenyl)-methoxycarbonyloxy]-1-(4-methyl-pent-3-enyl)-1-azonia-bicyclo[2.2.2]octane; bromide (compound 31)

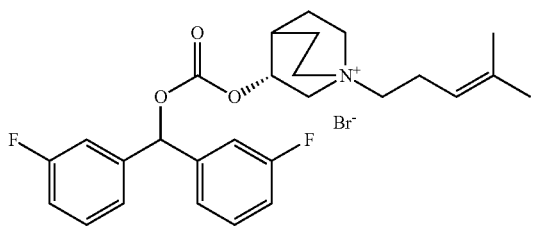 [SMILES: CC(C)=CCC[N+]12CCC(CC1)[C@@H](OC(=O)OC(c1cccc(F)c1)c1cccc(F)c1)C2 ; [Br-]]

The desired product was prepared by reacting (R)-1-azabicyclo[2.2.2]oct-3-yl ester bis-(3-fluoro-phenyl)-methyl ester with 5-bromo-2-methylpent-2-ene.

$^1$H NMR analysis (300 MHz, DMSO-$d_6$)

δ: 7.39-7.52 (m, 2H), 7.25-7.39 (m, 4H), 7.08-7.23 (m, 2H), 6.77 (s, 1H), 5.03-5.09 (m, 1H), 4.89-5.02 (m, 1H), 3.74-3.99 (m, 1H), 3.48-3.60 (m, 1H), 3.31-3.47 (m, 4H), 3.15 (t, 2H), 2.29-2.43 (m, 3H), 1.77-2.13 (m, 4H), 1.68 (s, 3H), 1.63 (s, 3H).

LC-MS (ESI POS): 456.00 (MH+).

Example 57

(R)-1-(2-Benzo[b]thiophen-2-yl-2-oxo-ethyl)-3-[bis-(3-fluoro-phenyl)-methoxycarbonyloxy]-1-azoniabicyclo[2.2.2]octane; bromide (compound 32)

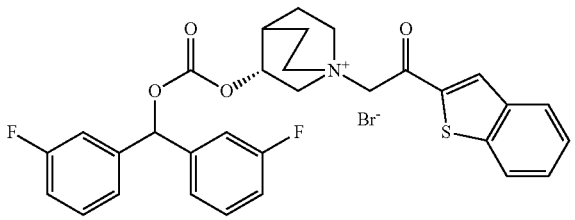 [SMILES: O=C(OC(c1cccc(F)c1)c1cccc(F)c1)O[C@H]1C[N+]2(CC(=O)c3cc4ccccc4s3)CCC1CC2 ; [Br-]]

The desired product was prepared by reacting (R)-1-azabicyclo[2.2.2]oct-3-yl ester bis-(3-fluoro-phenyl)-methyl ester with 1-benzo[b]thiophen-2-yl-2-bromo-ethanone.

$^1$H NMR analysis (300 MHz, DMSO-$d_6$)

δ: 8.50 (s, 1H), 8.01-8.26 (m, 2H), 7.58-7.67 (m, 1H), 7.51-7.58 (m, 1H), 7.40-7.51 (m, 2H), 7.26-7.40 (m, 4H), 7.08-7.24 (m, 2H), 6.79 (s, 1H), 5.19 (s, 2H), 5.10-5.17 (m, 1H), 4.09-4.26 (m, 1H), 3.81-3.93 (m, 1H), 3.57-3.81 (m, 4H), 2.32-2.47 (m, 1H), 1.84-2.19 (m, 4H).

LC-MS (ESI POS): 547.92 (MH+).

Example 58

(R)-1-Benzyl-3-[bis-(3-fluoro-phenyl)-methoxycarbonyloxy]-1-azonia-bicyclo[2.2.2]octane; bromide (compound 33)

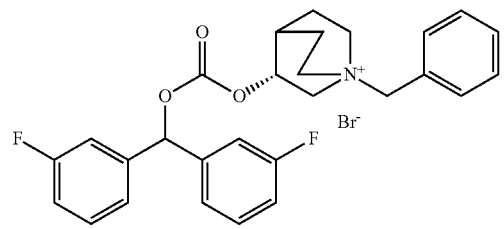 [SMILES: O=C(OC(c1cccc(F)c1)c1cccc(F)c1)O[C@H]1C[N+]2(Cc3ccccc3)CCC1CC2 ; [Br-]]

The desired product was prepared by reacting (R)-1-azabicyclo[2.2.2]oct-3-yl ester bis-(3-fluoro-phenyl)-methyl ester with bromomethyl-benzene.

$^1$H NMR analysis (300 MHz, DMSO-$d_6$)

δ: 7.39-7.60 (m, 7H), 7.24-7.37 (m, 4H), 7.11-7.24 (m, 2H), 6.77 (s, 1H), 4.86-5.18 (m, 1H), 4.51 (d, 1H), 4.45 (d, 1H), 3.68-3.84 (m, 1H), 3.52-3.65 (m, 1H), 3.41-3.52 (m, 2H), 3.32-3.38 (m, 2H), 2.30-2.41 (m, 1H), 1.63-2.16 (m, 4).

LC-MS (ESI POS): 463.98 (MH+).

Example 59

(R)-3-[Bis-(3-fluoro-phenyl)-methoxycarbonyloxy]-1-(2-phenoxy-ethyl)-1-azonia-bicyclo[2.2.2]octane; bromide (compound 34)

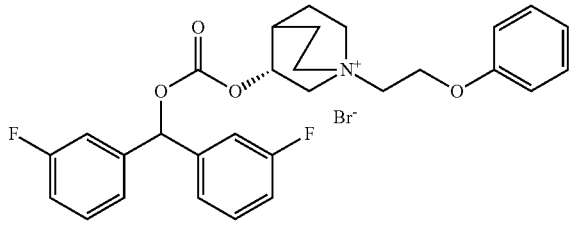 [SMILES: O=C(OC(c1cccc(F)c1)c1cccc(F)c1)O[C@H]1C[N+]2(CCOc3ccccc3)CCC1CC2 ; [Br-]]

The desired product was prepared by reacting (R)-1-azabicyclo[2.2.2]oct-3-yl ester bis-(3-fluoro-phenyl)-methyl ester with (2-bromoethoxy)benzene.

$^1$H NMR analysis (300 MHz, DMSO-$d_6$)

δ: 7.39-7.51 (m, 2H), 7.26-7.37 (m, 6H), 7.11-7.23 (m, 2H), 6.94-7.06 (m, 3H), 6.78 (s, 1H), 4.92-5.20 (m, 1H), 4.44 (br. s., 2H), 3.92-4.10 (m, 1H), 3.67-3.75 (m, 2H), 3.41-3.67 (m, 5H), 2.33-2.42 (m, 1H), 1.74-2.15 (m, 4H).

LC-MS (ESI POS): 493.97 (MH+).

Example 60

(R)-3-[Bis-(3-fluoro-phenyl)-methoxycarbonyloxy]-1-methyl-1-azonia-bicyclo[2.2.2]octane; iodide (compound 35)

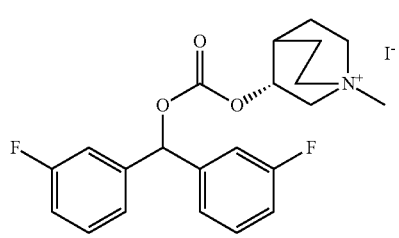 [SMILES: C[N+]12CCC(CC1)[C@@H](OC(=O)OC(c1cccc(F)c1)c1cccc(F)c1)C2 ; [I-]]

The desired product was prepared by reacting (R)-1-azabicyclo[2.2.2]oct-3-yl ester bis-(3-fluoro-phenyl)-methyl ester with methyl iodide.

$^1$H NMR analysis (300 MHz, DMSO-d$_6$)

δ: 7.40-7.52 (m, 2H), 7.25-7.37 (m, 4H), 7.10-7.25 (m, 2H), 6.77 (s, 1H), 4.87-5.16 (m, 1H), 3.84 (dd, 1H), 3.57 (dt, 1H), 3.32-3.50 (m, 4H), 2.96 (s, 3H), 2.32-2.40 (m, 1H), 1.63-2.21 (m, 4H).

LC-MS (ESI POS): 387.97 (MH+).

Example 61

Preparation of (R)-3-[bis-(3-fluoro-phenyl)-methoxycarbonyloxy]-1-(2-oxo-2-pyridin-4-yl-ethyl)-1-azonia-bicyclo[2.2.2]octane; bromide (compound 36)

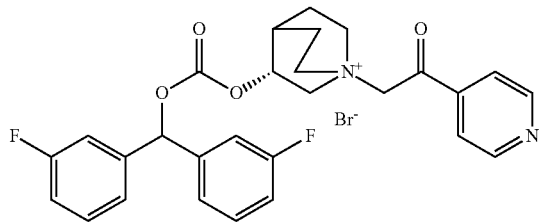 [SMILES: O=C(OC(c1cccc(F)c1)c1cccc(F)c1)O[C@H]1C[N+]2(CC(=O)c3ccncc3)CCC1CC2 ; [Br-]]

N,N-Diisopropylethylamine (0.037 mL, 0.22 mmol) was added to a solution of 2-bromo-1-(pyridin-4-yl)ethanone hydrobromide (60.2 mg, 0.22 mmol) dissolved in EtOAc (0.5 mL). After 10 minutes, a solution of (R)-bis(3-fluorophenyl)methyl quinuclidin-3-yl carbonate (80 mg, 0.22 mmol), obtained as described in Example 2, in EtOAc (0.5 mL) was added, and the reaction mixture was stirred at room temperature for 2 hours. Et$_2$O (1 mL) was added, and the precipitate was collected by suction filtration. The solid was dissolved in water and extracted with DCM. The organic phase was dried over anhydrous sodium sulfate and filtered, and the solvent was evaporated under reduced pressure to give the desired compound as a pink solid (76 mg; 62% yield).

$^1$H NMR analysis (300 MHz, DMSO-d$_6$)

δ: 8.47-9.13 (m, 2H), 7.67-7.95 (m, 2H), 7.39-7.56 (m, 2H), 7.25-7.39 (m, 4H), 7.06-7.25 (m, 2H), 6.78 (s, 1H), 5.19 (s, 2H), 5.07-5.18 (m, 1H), 4.00-4.30 (m, 1H), 3.47-3.89 (m, 5H), 2.39-2.46 (m, 1H), 1.88-2.22 (m, 4H).

LC-MS (ESI POS): 492.97 (MH+).

Example 62

(R)-3-[(2-Fluoro-phenyl)-(3-fluoro-phenyl)-methoxycarbonyloxy]-1-(2-oxo-2-thiophen-2-yl-ethyl)-1-azonia-bicyclo[2.2.2]octane; chloride (compound 37)

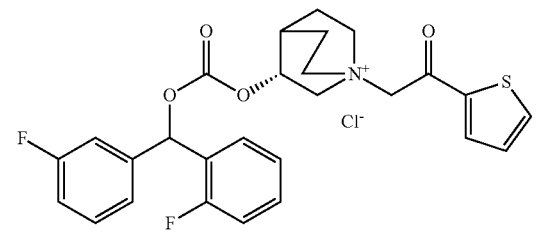 [SMILES: O=C(OC(c1cccc(F)c1)c1ccccc1F)O[C@H]1C[N+]2(CC(=O)c3cccs3)CCC1CC2 ; [Cl-]]

The desired product was prepared by reacting carbonic acid (R)-(1-aza-bicyclo[2.2.2]oct-3-yl)ester (3-fluoro-phenyl)-(2-fluoro-phenyl)-methyl ester with 2-(2-chloro)acetylthiophene.

$^1$H NMR analysis (300 MHz, DMSO-d$_6$)

δ: 8.21 (d, 1H), 7.97-8.15 (m, 1H), 7.10-7.59 (m, 9H), 6.93 (s, 1H), 5.12-5.27 (m, 1H), 5.07 (s, 2H), 4.05-4.28 (m, 1H), 3.52-3.95 (m, 5H), 2.38-2.46 (m, 1H), 1.71-2.18 (m, 4H).

LC-MS (ESI POS): 498.02 (MH+).

Example 63

(R)-3-[Bis-(2-chloro-phenyl)-methoxycarbonyloxy]-1-(2-oxo-2-thiophen-2-yl-ethyl)-1-azonia-bicyclo[2.2.2]octane; chloride (compound 38)

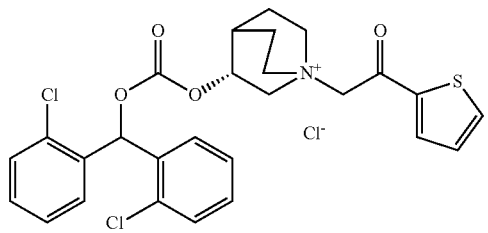 [SMILES: O=C(OC(c1ccccc1Cl)c1ccccc1Cl)O[C@H]1C[N+]2(CC(=O)c3cccs3)CCC1CC2 ; [Cl-]]

The desired product was prepared by reacting carbonic acid (R)-(1-aza-bicyclo[2.2.2]oct-3-yl)ester bis-(2-chlorophenyl)-methyl ester with 2-(2-chloro)acetylthiophene.

$^1$H NMR analysis (300 MHz, DMSO-d$_6$)

δ: 8.21 (dd, 1H), 8.09 (dd, 1H), 7.52-7.69 (m, 2H), 7.39-7.53 (m, 4H), 4H), 7.27-7.39 (m, 3H), 7.26 (s, 1H), 5.12-5.29 (m, 1H), 5.09 (s, 2H), 4.15 (dd, 1H), 3.45-3.95 (m, 5H), 2.45 (br. s., 1H), 1.86-2.17 (m, 4H).

LC-MS (ESI POS): 529.96 (MH+).

Example 64

(R)-1-(2-Oxo-2-thiophen-2-yl-ethyl)-3-(phenyl-o-tolyl-methoxycarbonyloxy)-1-azonia-bicyclo[2.2.2]octane; chloride (compound 39)

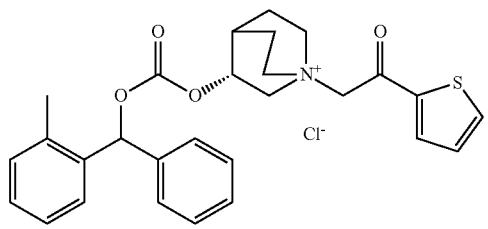 [SMILES: Cc1ccccc1C(OC(=O)O[C@H]1C[N+]2(CC(=O)c3cccs3)CCC1CC2)c1ccccc1 ; [Cl-]]

The desired product was prepared by reacting carbonic acid (R)-(1-aza-bicyclo[2.2.2]oct-3-yl)ester phenyl-o-tolyl-methyl ester with 2-(2-chloro)acetylthiophene.

$^1$H NMR analysis (300 MHz, DMSO-d$_6$)

δ: 8.21 (d, 1H), 7.99-8.14 (m, 1H), 7.12-7.53 (m, 10H), 6.85 (s, 1H), 5.09-5.21 (m, 1H), 5.07 (s, 2H), 3.94-4.23 (m, 1H), 3.44-3.90 (m, 5H), 2.34-2.47 (m, 1H), 2.29 (s, 3H), 1.77-2.16 (m, 4H).

LC-MS (ESI POS): 476.08 (MH+).

Example 65

(R)-3-[(3-Fluoro-phenyl)-(3-methoxy-phenyl)-methoxycarbonyloxy]-1-(2-oxo-2-thiophen-2-yl-ethyl)-1-azonia-bicyclo[2.2.2]octane; chloride (compound 40)

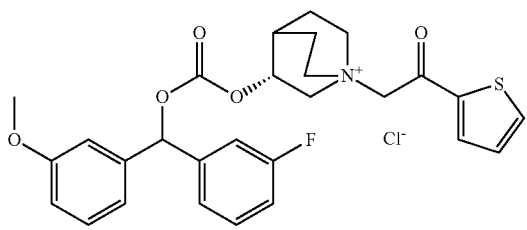 [SMILES: COc1cccc(C(OC(=O)O[C@H]2C[N+]3(CC(=O)c4cccs4)CCC2CC3)c2cccc(F)c2)c1 ; [Cl-]]

The desired product was prepared by reacting carbonic acid (R)-(1-aza-bicyclo[2.2.2]oct-3-yl)ester (3-fluoro-phenyl)-(3-methoxy-phenyl)-methyl ester with 2-(2-chloro)acetylthiophene.

$^1$H NMR analysis (300 MHz, DMSO-$d_6$)

δ: 8.21 (dd, 1H), 8.09 (d, 1H), 7.38-7.51 (m, 1H), 7.24-7.38 (m, 4H), 7.09-7.22 (m, 1H), 6.97-7.06 (m, 2H), 6.84-6.95 (m, 1H), 6.72 (s, 1H), 5.12-5.20 (m, 1H), 5.09 (s, 2H), 4.06-4.22 (m, 1H), 3.78-3.89 (m, 1H), 3.76 and 3.75 (s, 3H), 3.52-3.73 (m, 4H), 2.36-2.46 (m, 1H), 1.84-2.18 (m, 4H).

LC-MS (ESI POS): 510.08 (MH+).

Example 66

(R)-3-[Cyclohexyl-(3-fluoro-phenyl)-methoxycarbonyloxy]-1-(2-oxo-2-thiophen-2-yl-ethyl)-1-azonia-bicyclo[2.2.2]octane; chloride (compound 41)

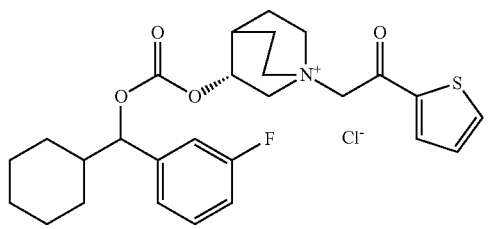 [SMILES: O=C(OC(c1cccc(F)c1)C1CCCCC1)O[C@H]1C[N+]2(CC(=O)c3cccs3)CCC1CC2 ; [Cl-]]

The desired product was prepared by reacting carbonic acid (R)-(1-aza-bicyclo[2.2.2]oct-3-yl)ester cyclohexyl-(3-fluoro-phenyl)-methyl ester with 2-(2-chloro)acetylthiophene.

$^1$H NMR analysis (300 MHz, DMSO-$d_6$)

δ: 8.12-8.31 (m, 1H), 7.88-8.15 (m, 1H), 7.29-7.53 (m, 2H), 6.96-7.24 (m, 3H), 5.30-5.47 (m, 1H), 5.02-5.20 (m, 3H), 3.99-4.25 (m, 1H), 3.47-3.89 (m, 5H), 1.45-2.21 (m, 9H), 0.79-1.45 (m, 7H).

LC-MS (ESI POS): 486.11 (MH+).

Example 67

(R)-3-[(3-Chloro-phenyl)-(3-fluoro-phenyl)-methoxycarbonyloxy]-1-(2-oxo-2-thiophen-2-yl-ethyl)-1-azonia-bicyclo[2.2.2]octane; chloride (compound 42)

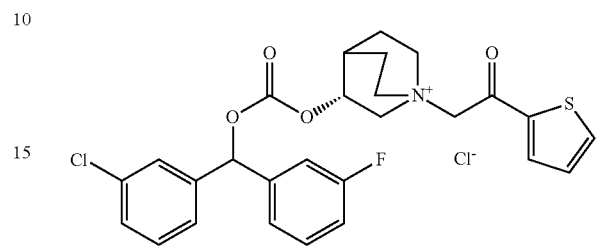

The desired product was prepared by reacting carbonic acid (R)-(1-aza-bicyclo[2.2.2]oct-3-yl)ester (3-chloro-phenyl)-(3-fluoro-phenyl)-methyl ester with 2-(2-chloro)acetylthiophene.

$^1$H NMR analysis (300 MHz, DMSO-$d_6$)

δ: 8.21 (dd, 1H), 8.08 (dd, 1H), 7.52-7.61 (m, 1H), 7.26-7.51 (m, 7H), 7.11-7.23 (m, 1H), 6.78 (s, 1H), 5.11-5.20 (m, 1H), 5.06 (s, 2H), 4.04-4.23 (m, 1H), 3.78-3.89 (m, 1H), 3.51-3.78 (m, 4H), 2.37-2.46 (m, 1H), 1.69-2.21 (m, 4H).

LC-MS (ESI POS): 514.05 (MH+).

Example 68

(R)-3-[(3,5-Difluoro-phenyl)-(3-fluoro-phenyl)-methoxycarbonyloxy]-1-(2-oxo-2-thiophen-2-yl-ethyl)-1-azonia-bicyclo[2.2.2]octane; chloride (compound 43)

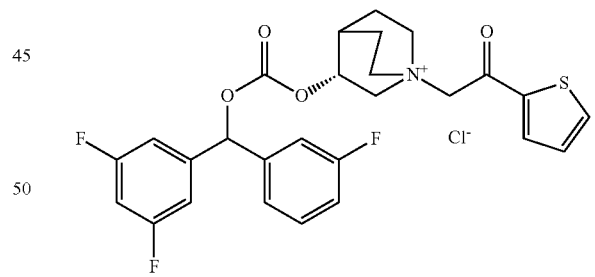

The desired product was prepared by reacting carbonic acid (R)-(1-aza-bicyclo[2.2.2]oct-3-yl)ester (3,5-difluoro-phenyl)-(3-fluoro-phenyl)-methyl ester with 2-(2-chloro)acetylthiophene.

$^1$H NMR analysis (300 MHz, DMSO-$d_6$)

δ: 8.21 (dd, 1H), 8.08 (dd, 1H), 7.39-7.60 (m, 2H), 7.31-7.39 (m, 1H), 7.12-7.29 (m, 5H), 7.02 (s, 1H), 5.11-5.26 (m, 1H), 5.06 (s, 2H), 4.04-4.27 (m, 1H), 3.48-3.96 (m, 5H), 2.33-2.45 (m, 1H), 1.83-2.22 (m, 4H).

LC-MS (ESI POS): 515.8 (MH+).

Example 69

(R)-3-[(3-Fluoro-phenyl)-m-tolyl-methoxycarbonyloxy]-1-(2-oxo-2-thiophen-2-yl-ethyl)-1-azonia-bicyclo[2.2.2]octane; chloride (compound 44)

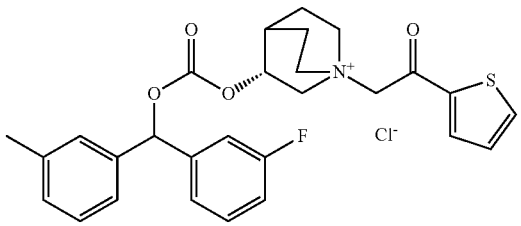 [SMILES: Cc1cccc(C(OC(=O)O[C@H]2C[N+]3(CC(=O)c4cccs4)CCC2CC3)c2cccc(F)c2)c1 ; [Cl-]]

The desired product was prepared by reacting carbonic acid (R)-(1-aza-bicyclo[2.2.2]oct-3-yl)ester (3-fluoro-phenyl)-m-tolyl-methyl ester with 2-(2-chloro)acetylthiophene.

$^1$H NMR analysis (300 MHz, DMSO-$d_6$)

δ: 8.21 (d, 1H), 8.08 (d, 1H), 7.39-7.52 (m, 1H), 7.04-7.38 (m, 8H), 6.71 (s, 1H), 5.13 (m, 1H), 5.06 (s, 2H), 4.02-4.23 (m, 1H), 3.50-3.92 (m, 5H), 2.39-2.46 (m, 1H), 2.31 (s, 3H), 1.76-2.18 (m, 4H).

LC-MS (ESI POS): 494.05 (MH+).

Example 70

(R)-3-[(3-Fluoro-phenyl)-(4-methylsulfanyl-phenyl)-methoxycarbonyloxy]-1-(2-oxo-2-thiophen-2-yl-ethyl)-1-azonia-bicyclo[2.2.2]octane; chloride (compound 45)

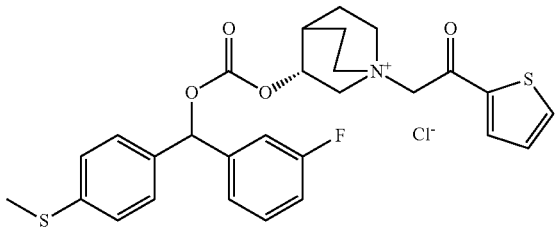 [SMILES: CSc1ccc(C(OC(=O)O[C@H]2C[N+]3(CC(=O)c4cccs4)CCC2CC3)c2cccc(F)c2)cc1 ; [Cl-]]

The desired product was prepared by reacting carbonic acid (R)-(1-aza-bicyclo[2.2.2]oct-3-yl)ester (3-fluoro-phenyl)-(4-methylsulfanyl-phenyl)-methyl ester with 2-(2-chloro)acetylthiophene.

1H NMR analysis (300 MHz, DMSO-$d_6$)

δ: 8.21 (dd, 1H), 8.09 (d, 1H), 7.32-7.59 (m, 4H), 7.22-7.32 (m, 4H), 7.09-7.22 (m, 1H), 6.73 (s, 1H), 5.11-5.19 (m, 1H), 5.09 (s, 2H), 4.05-4.23 (m, 1H), 3.51-3.89 (m, 5H), 2.46 (s, 3H), 2.37-2.44 (m, 1H), 1.79-2.14 (m, 4H).

LC-MS (ESI POS): 525.91 (MH+).

Example 71

(R)-3-[(3-Fluoro-phenyl)-(4-fluoro-phenyl)-methoxycarbonyloxy]-1-(2-oxo-2-thiophen-2-yl-ethyl)-1-azonia-bicyclo[2.2.2]octane; chloride (compound 46)

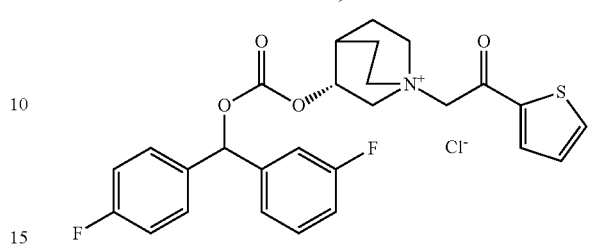

The desired product was prepared by reacting carbonic acid (R)-(1-aza-bicyclo[2.2.2]oct-3-yl)ester (4-fluoro-phenyl)-(3-fluoro-phenyl)-methyl ester with 2-(2-chloro)acetylthiophene.

NMR analysis (300 MHz, DMSO-$d_6$)

δ: 8.21 (dd, 1H), 8.08 (dd, 1H), 7.40-7.58 (m, 3H), 7.35 (dd, 1H), 7.08-7.33 (m, 5H), 6.78 (s, 1H), 5.10-5.19 (m, 1H), 5.05 (s, 2H), 3.97-4.23 (m, 1H), 3.50-3.89 (m, 5H), 2.33-2.46 (m, 1H), 1.88-2.17 (m, 4H).

LC-MS (ESI POS): 497.91 (MH+).

Example 72

(R)-3-[(3,4-Difluoro-phenyl)-phenyl-methoxycarbonyloxy]-1-(2-oxo-2-thiophen-2-yl-ethyl)-1-azonia-bicyclo[2.2.2]octane; chloride (compound 47)

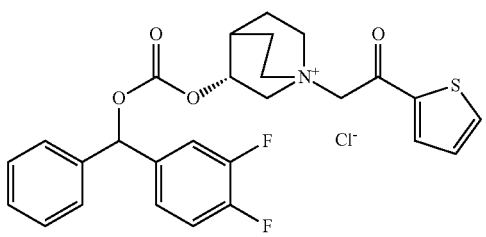 [SMILES: O=C(OC(c1ccccc1)c1ccc(F)c(F)c1)O[C@H]1C[N+]2(CC(=O)c3cccs3)CCC1CC2 ; [Cl-]]

The desired product was prepared by reacting carbonic acid (R)-(1-aza-bicyclo[2.2.2]oct-3-yl)ester (3,4-difluoro-phenyl)-phenyl-methyl ester with 2-(2-chloro)acetylthiophene.

$^1$H NMR analysis (300 MHz, DMSO-$d_6$)

δ: 8.21 (ddd, 1H), 8.01-8.13 (m, 1H), 7.49-7.64 (m, 1H), 7.21-7.49 (m, 8H), 6.76 (s, 1H), 5.11-5.21 (m, 1H), 5.09 (s, 2H), 4.02-4.28 (m, 1H), 3.46-3.92 (m, 5H), 2.33-2.46 (m, 1H), 1.69-2.17 (m, 4H).

LC-MS (ESI POS): 497.90 (MH+).

Example 73

(R)-3-[(3-Fluoro-phenyl)-phenyl-methoxycarbonyloxy]-1-(2-oxo-2-thiophen-2-yl-ethyl)-1-azonia-bicyclo[2.2.2]octane; chloride (compound 48)

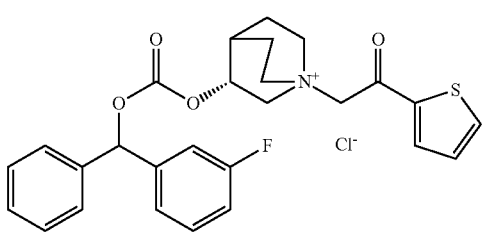 [SMILES: O=C(OC(c1ccccc1)c1cccc(F)c1)O[C@H]1C[N+]2(CC(=O)c3cccs3)CCC1CC2 ; [Cl-]]

The desired product was prepared by reacting carbonic acid (R)-(1-aza-bicyclo[2.2.2]oct-3-yl)ester (3-fluoro-phenyl)-phenyl-methyl ester with 2-(2-chloro)acetylthiophene.

$^1$H NMR analysis (300 MHz, DMSO-$d_6$)

δ: 8.21 (dd, 1H), 8.08 (ddd, 1H), 7.22-7.54 (m, 9H), 7.00-7.23 (m, 1H), 6.76 (s, 1H), 5.11-5.22 (m, 1H), 5.06 (s, 2H), 4.01-4.22 (m, 1H), 3.47-3.92 (m, 5H), 2.36-2.45 (m, 1H), 1.70-2.17 (m, 4H).

LC-MS (ESI POS): 479.94 (MH+).

Legend
*NMR
s=singlet
d=doublet
t=triplet
q=quartet
dd=doublet of doublets
m=multiplet
br=broad Biological Characterization.

The interaction with M3 muscarinic receptors can be estimated by the results of in vitro studies which evaluated the M3/M2 binding assays, the potency of the test compounds, and the offset of the inhibitory activity produced after washout of the antagonists in isolated guinea pig trachea and by the in vivo duration of action against acetylcholine-induced bronchospasm in the guinea pig.

Example 74

M3/M2 Binding Assays

CHO-K1 clone cells expressing the human M2 or M3-receptors (Swissprot P08172, P20309 respectively) were harvested in Ca$^{++}$/Mg$^{++}$ free phosphate-buffered saline and collected by centrifugation at 1500 rpm for 3 minutes. The pellets were resuspended in ice cold buffer A (15 mM Tris-HCl pH 7.4, 2 mM MgCl$_2$, 0.3 mM EDTA, 1 mM EGTA) and homogenized by a PBI politron (setting 5 for 15 s). The crude membrane fraction was collected by two consecutive centrifugation steps at 40000 g for 20 minutes at 4° C., and separated by a washing step in buffer A. The pellets obtained were finally re-suspended in buffer B (75 mM Tris HCl pH 7.4, 12.5 mM MgCl$_2$, 0.3 mM EDTA, 1 mM EGTA, 250 mM sucrose), and aliquots were stored at −80° C.

The day of experiment, frozen membranes were re-suspended in buffer C (50 mM Tris-HCl pH 7.4, 2.5 mM MgCl$_2$, 1 mM EDTA). The non-selective muscarinic radioligand [$^3$H]-N-methyl scopolamine (*Mol. Pharmacol.* 45:899-907) was used to label the M2, and M3 binding sites. Binding experiments were performed in duplicate (ten point concentrations curves) in 96 well plates at radioligand concentration of 0.1-0.3 nM. The non-specific binding was determined in the presence of cold N-methyl scopolamine 10 μM. Samples (final volume 0.75 ml) were incubated at room temperature for 60 minutes for M2 and 90 minutes for M3 binding assay. The reaction was terminated by rapid filtration through GF/B Unifilter plates and two washes (0.75 ml) with cold buffer C using a Packard Filtermate Harvester. Radioactivity on the filters was measured by a microplate scintillation counter TriCarb 2500 (PerkinElmer).

Example 75

In vitro Interaction with the M3 Receptors

The potency of the antagonist activity in isolated guinea pig trachea was investigated following a method previously described by Haddad, E. B., et al. in *Br. J. Pharmacol.*, vol. 127, pp. 413-420 (1999), with few modifications. A cumulative concentration-response curve to test antagonists was constructed on preparations pre-contracted by carbachol, until a complete inhibition of smooth muscle tone was achieved. The concentration of antagonist producing a 50% reversal of carbachol-induced tonic contraction (IC$_{50}$) was taken as a measure of its potency in this bioassay.

In the experiments aiming at assessing the offset of the inhibitory effects produced by test compounds, the minimal concentration of the test compounds known to produce a maximal inhibitory effect was administered to carbachol-pre-contracted preparations. As soon as the tonic contraction was completely reversed, the organ bath solution was renewed and preparations were thoroughly washed with fresh Krebs solution. Carbachol (0.3 μM) was administered again (at 30 minute interval between washout and next administration) during the next 4 hours.

After the administration of carbachol, the inhibitory effects of the compounds of the invention, administered at a concentration of 10 nM, were expressed as percentage of the recovery of the contracting response to carbachol. The percentage of recovery four hours after the washout was lower than 50%.

The values of inhibitory M3 activity tested on compounds 1, 2, 3, 4, 5, 6, 7, 9, 11, 12, 13, 14, 15, 17, and 18 to 48 were between 0.05 and 414 nM.

Example 76

In vivo Studies

The in vivo tests on acetylcholine-induced bronchospasm in guinea pig were performed according to Konzett, H. and Rössler, F., *Arch. Exp. Path. Pharmacol.*, vol. 195, pp. 71-74 (1940). Aqueous solutions of the test compounds were instilled intratracheally in anaesthetized mechanically ventilated guinea pigs. Bronchial response to intravenous acetylcholine challenge was determined before and after drug administration and changes in pulmonary resistance at several time-points were expressed as percent of inhibition of bronchospasm. The bronchodilator activity of the tested compounds persisted unchanged up to 24 hours after the administration.

Example 77

Plasma Stability of (Compound 1)

In order to demonstrate that the compounds are degraded, stability in rat and human plasma at 1 and 5 hours was tested for a representative compound of the invention, which is compound 1. Briefly 10 μl of a stock solution 250 μM of compound 1 in acetonitrile were added to 1 ml of rat and human plasma, and samples were incubated at 37° C. Plasma (50 μL) was taken after 0, 1 and 5 hours of incubation and added to 140 μl of acetonitrile with addition of verapamil as internal standard (250 ng/ml). Samples were analysed by HPLC-MS/MS analysis.

Plasma stability was calculated as percentage remaining after 1 and 5 hours by dividing the peak area at 1 or 5 hours by the area of the peak at time 0. After 1 and 5 hours of incubation, less than 2% of compound 1 was detected, indicating that compound 1 is very unstable in both plasma species. The other compounds of the invention behave similarly.

Where a numerical limit or range is stated herein, the endpoints are included. Also, all values and subranges within a numerical limit or range are specifically included as if explicitly written out.

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A method for the treatment of a broncho-obstructive disease, comprising administering, to a subject in need thereof, an effective amount of a salt represented by formula (I):

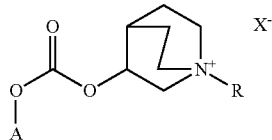

(I)

wherein:

A is an optionally substituted aryl group, optionally substituted heteroaryl group, optionally substituted arylalkyl group, optionally substituted heteroarylalkyl group, or a group of formula (a)

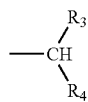

(a)

wherein:

$R_3$ and $R_4$ are the same or different and are independently selected from the group consisting of H, $(C_3-C_8)$-cycloalkyl, aryl or heteroaryl, wherein said aryl or heteroaryl may be optionally substituted with a halogen atom or with one or more substituents independently selected from the group consisting of OH, O—$(C_1-C_{10})$-alkyl, oxo, SH, S—$(C_1-C_{10})$-alkyl, $NO_2$, CN, $CONH_2$, COOH, $(C_1-C_{10})$-alkoxycarbonyl, $(C_1-C_{10})$-alkylsulfanyl, $C_1-C_{10}$)-alkylsulfinyl, $(C_1-C_{10})$-alkylsulfonyl, $(C_1-C_{10})$-alkyl, and $(C_1-C_{10})$-alkoxyl, or when $R_3$ and $R_4$ are both independently aryl or heteroaryl they may be linked through a Y group which is a $(CH_2)_n$ group wherein n=0-2, wherein when n=0, Y is a single bond, forming a tricyclic ring system wherein a carbon atom of $(CH_2)_n$ may be substituted by a heteroatom selected from O, S, N, and with the proviso that $R_3$ and $R_4$ are never both H;

R is a group selected from the group consisting of:

$(C_1-C_{10})$-alkyl, $(C_2-C_{10})$-alkenyl, and $(C_2-C_{10})$-alkynyl each of which may be optionally substituted with a group selected from the group consisting of:

$NH_2$, $NR_1R_2$, $CONR_1R_2$, $NR_2COR_1$, OH, $SOR_1$, $SO_2R_1$, SH, CN, $NO_2$, an alicyclic compound, Z—$R_1$, wherein Z is selected from CO, O, COO, OCO, $SO_2$, S, SO, COS, and SCO or it is a bond, and $(C_3-C_8)$-cycloalkyl;

$R_1$ is a group selected from the group consisting of:

an alicyclic compound optionally substituted with one or more substituents independently selected from the group consisting of OH, oxo, SH, $NO_2$, CN, $CONH_2$, $NR_2CO$—$(C_1-C_x)$-alkyl, COOH, $(C_1-C_{10})$-alkoxycarbonyl, $(C_1-C_{10})$-alkylsulfanyl, $(C_1-C_{10})$-alkylsulfinyl, $(C_1-C_{10})$-alkylsulfonyl, $(C_1-C_{10})$-alkyl, and $(C_1-C_{10})$-alkoxyl $NR_2CO$—$(C_1-C_{10})$-alkyl;

an aryl group optionally substituted with $NR_2CO$—$(C_1-C_{10})$-alkyl; and a heteroaryl group optionally substituted with a group selected from the group consisting of $NR_2CO$—$(C_1-C_{10})$-alkyl, $(C_1-C_{10})$-alkyl, O—$(C_1-C_{10})$-alkyl, and halogen;

$R_2$ is a group selected from the group consisting of H, phenoxycarbonyl, benzyloxycarbonyl, $(C_1-C_{10})$-alkoxycarbonyl, $(C_1-C_{10})$-alkylcarbonyl, $(C_1-C_{10})$-alkylsulfonyl; and $(C_1-C_{10})$-alkyl; and $X^-$ is a physiologically acceptable anion.

2. A method for the treatment of asthma, chronic bronchitis, or chronic obstructive pulmonary disease, comprising administering, to a subject in need thereof, an effective amount of a salt represented by formula (I):

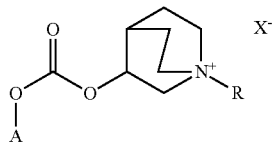

(I)

wherein:

A is an optionally substituted aryl group, optionally substituted heteroaryl group, optionally substituted arylalkyl group, optionally substituted heteroarylalkyl group, or a group of formula (a)

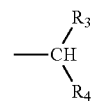

(a)

wherein:

$R_3$ and $R_4$ are the same or different and are independently selected from the group consisting of H, $(C_3-C_8)$-cycloalkyl, aryl or heteroaryl, wherein said aryl or heteroaryl may be optionally substituted with a halogen atom or with one or more substituents independently selected from the group consisting of OH, O—$(C_1-C_{10})$-alkyl, oxo, SH, S—$(C_1-C_{10})$-alkyl, $NO_2$, CN, $CONH_2$, COOH, $(C_1-C_{10})$-alkoxycarbonyl, $(C_1-C_{10})$-alkylsulfanyl, $(C_1-C_{10})$-alkylsulfinyl, $(C_1-C_{10})$-alkylsulfonyl, $(C_1-C_{10})$-alkyl, and $(C_1-C_{10})$-alkoxyl, or when $R_3$ and $R_4$ are both independently aryl or heteroaryl they may be linked through a Y group which is a $(CH_2)_n$ group wherein n=0-2, wherein when n=0, Y is a single bond, forming a tricyclic ring system wherein a carbon atom of $(CH_2)_n$ may be substituted by a heteroatom selected from O, S, N, and with the proviso that $R_3$ and $R_4$ are never both H;

R is a group selected from the group consisting of:

$(C_1-C_{10})$-alkyl, $(C_2-C_{10})$-alkenyl, and $(C_2-C_{10})$-alkynyl each of which may be optionally substituted with a group selected from the group consisting of:

$NH_2$, $NR_1R_2$, $CONR_1R_2$, $NR_2COR_1$, OH, $SOR_1$, $SO_2R_1$, SH, CN, $NO_2$, an alicyclic compound, Z—$R_1$, wherein Z is selected from CO, O, COO, OCO, $SO_2$, S, SO, COS, and SCO or it is a bond, and $(C_3-C_8)$-cycloalkyl;

R₁ is a group selected from the group consisting of:

an alicyclic compound optionally substituted with one or more substituents independently selected from the group consisting of OH, oxo, SH, $NO_2$, CN, $CONH_2$, $NR_2CO$—$(C_1$-$C_x)$-alkyl, COOH, $(C_1$-$C_{10})$-alkoxycarbonyl, $(C_1$-$C_{10})$-alkylsulfanyl, $(C_1$-$C_{10})$-alkylsulfinyl, $(C_1$-$C_{10})$-alkylsulfonyl, $(C_1$-$C_{10})$-alkyl, and $(C_1$-$C_{10})$-alkoxyl $NR_2CO$—$(C_1$-$C_{10})$-alkyl;

an aryl group optionally substituted with $NR_2CO$—$(C_1$-$C_{10})$-alkyl; and a heteroaryl group optionally substituted with a group selected from the group consisting of $NR_2CO$—$(C_1$-$C_{10})$-alkyl, $(C_1$-$C_{10})$-alkyl, O—$(C_1$-$C_{10})$-alkyl, and halogen;

$R_2$ is a group selected from the group consisting of H, phenoxycarbonyl, benzyloxycarbonyl, $(C_1$-$C_{10})$-alkoxycarbonyl, $(C_1$-$C_{10})$-alkylcarbonyl, $(C_1$-$C_{10})$-alkylsulfonyl; and $(C_1$-$C_{10})$-alkyl; and $X^-$ is a physiologically acceptable anion.

3. A method according to claim 2, wherein R is $(C_1$-$C_6)$-alkyl substituted by —Z—$R_1$.

4. A method according to claim 2, wherein R is $(C_1$-$C_6)$-alkyl substituted by —Z—$R_1$, wherein Z is O, CO, or a bond, and $R_1$ is aryl or heteroaryl, optionally substituted with one or more halogen atoms.

5. A method according to claim 2, wherein R is $CH_2$—Z—$R_1$, wherein Z is CO and $R_1$ is thienyl, according to formula (II):

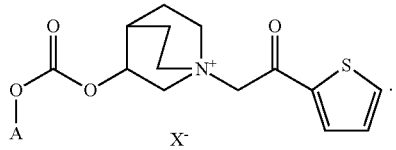

(II)

6. A method according to claim 5, wherein A is optionally substituted aryl, optionally substituted heteroaryl, optionally substituted arylalkyl, optionally substituted heteroarylalkyl, or a group of formula (a)

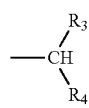

(a)

wherein $R_3$ and $R_4$ are both independently aryl, optionally substituted with one or more halogen atoms, or heteroaryl, optionally substituted with one or more halogen atoms.

7. A method according to claim 5, wherein A is a group of formula (a) wherein $R_3$ and $R_4$ are both phenyl, optionally substituted with one or more halogen atoms.

8. A method according to claim 5, wherein A is a group of formula (a) wherein $R_3$ and $R_4$ are both independently phenyl and they are linked through a Y group which is a $(CH_2)_n$ with n=0-2, wherein when n=0, Y is a single bond, forming a tricyclic ring system of formula (b)

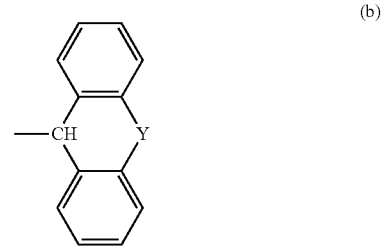

(b)

wherein a carbon atom of $(CH_2)_n$ may be substituted by a heteroatom selected from the group consisting of O, S, and N.

9. A method according to claim 5, wherein A is a 9H-fluoren-9-yl group, optionally substituted with one or more halogen atoms.

10. A method according to claim 5, wherein A is a benzyl group, optionally substituted with one or more halogen atoms.

11. A method according to claim 5, wherein A is a biphenylmethyl group, optionally substituted with one or more halogen atoms.

12. A method according to claim 5, wherein A is a thiophenylmethyl group, optionally substituted with one or more halogen atoms.

13. A method according to claim 2, wherein R is a propyl group, substituted with a Z—$R_1$ group, wherein Z is O and $R_1$ is phenyl, according to formula (III):

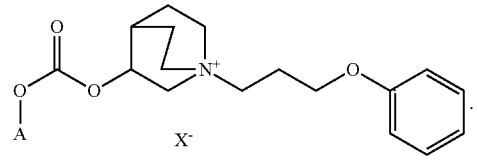

(III)

14. A method according to claim 13, wherein A is aryl, heteroaryl, arylalkyl, heteroarylalkyl, or a group of formula (a) wherein $R_3$ and $R_4$ are both independently aryl, optionally substituted with one or more halogen atoms, or heteroaryl, optionally substituted with one or more halogen atoms.

15. A method according to claim 13, wherein A is a group of formula (a) wherein R and $R_4$ are both phenyl, optionally substituted with one or more halogen atoms.

16. A method according to claim 13, wherein A is a group of formula (a) wherein $R_3$ and $R_4$ are both independently aryl or heteroaryl, and they are linked through a Y group which is $(CH_2)_n$ with n=0-2, wherein when n=0, Y is a single bond, forming a tricyclic ring system of formula (b)

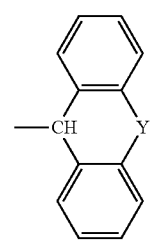

(b)

wherein a carbon atom of $(CH_2)_n$ may be substituted by a heteroatom selected from the group consisting of O, S, and N.

17. A method according to claim 13, wherein A is a 9H-fluoren-9-yl group, optionally substituted with one or more halogen atoms.

18. A method according to claim 13, wherein A is a benzyl group, optionally substituted with one or more halogen atoms.

19. A method according to claim 13, wherein A is a biphenylmethyl group, optionally substituted with one or more halogen atoms.

20. A method according to claim 13, wherein A is a thiophenylmethyl group, optionally substituted with one or more halogen atoms.

* * * * *